(12) United States Patent
Monia et al.

(10) Patent No.: US 9,150,864 B2
(45) Date of Patent: Oct. 6, 2015

(54) METHODS FOR MODULATING FACTOR 12 EXPRESSION

(75) Inventors: Brett P. Monia, Encinitas, CA (US); Robert A. MacLeod, Carlsbad, CA (US); Jeffrey R. Crosby, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/884,067

(22) PCT Filed: Nov. 8, 2011

(86) PCT No.: PCT/US2011/059804
§ 371 (c)(1),
(2), (4) Date: Aug. 21, 2013

(87) PCT Pub. No.: WO2012/064758
PCT Pub. Date: May 18, 2012

(65) Prior Publication Data
US 2013/0331434 A1     Dec. 12, 2013

Related U.S. Application Data

(60) Provisional application No. 61/411,309, filed on Nov. 8, 2010.

(51) Int. Cl.
*C07H 21/04*     (2006.01)
*C12N 15/113*    (2010.01)

(52) U.S. Cl.
CPC .......... *C12N 15/1137* (2013.01); *C12N 15/113* (2013.01); *C12N 2310/11* (2013.01); *C12N 2310/315* (2013.01); *C12N 2310/3341* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 5,801,154 | A | 9/1998 | Baracchini et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 2001/0053519 | A1 | 12/2001 | Fodor et al. |
| 2003/0228597 | A1 | 12/2003 | Cowsert et al. |
| 2004/0171570 | A1 | 9/2004 | Allerson et al. |
| 2005/0130923 | A1 | 6/2005 | Bhat et al. |
| 2007/0031844 | A1 | 2/2007 | Khvorova et al. |
| 2007/0299028 | A1* | 12/2007 | Siwkowski et al. ............. 514/44 |
| 2008/0039618 | A1 | 2/2008 | Allerson et al. |
| 2008/0254039 | A1* | 10/2008 | Nieswandt et al. ........ 424/158.1 |
| 2009/0012281 | A1 | 1/2009 | Swayze et al. |
| 2009/0064350 | A1* | 3/2009 | Dewald .............................. 800/3 |
| 2010/0137414 | A1* | 6/2010 | Freier et al. .................. 514/44 R |
| 2010/0324114 | A1 | 12/2010 | Dewald |
| 2011/0067124 | A1 | 3/2011 | Dewald |
| 2012/0309035 | A1 | 12/2012 | Lindahl et al. |
| 2013/0331434 | A1 | 12/2013 | Monia et al. |

FOREIGN PATENT DOCUMENTS

| | | |
|---|---|---|
| WO | WO 99/14226 | 3/1999 |
| WO | WO 03/004602 | 1/2003 |
| WO | WO 2004/106356 | 12/2004 |
| WO | WO 2005/021570 | 3/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/115478 | 9/2009 |
| WO | WO 2010/094732 | 8/2010 |
| WO | WO 2010/111702 | 9/2010 |
| WO | WO 2012/064758 | 5/2012 |
| WO | WO 2012/170947 | 12/2012 |

OTHER PUBLICATIONS

Weintraub (Scientific American 1990).*
Bennett et al. (Antisense & Nucleic Acid Drug Development 12:215-224 (2002).*
Bouillet et al. "Disease expression in women with hereditary angioedema" Am. J. Obstet. Gynecol. (2008) 199: 484.e1-484.e4.
Cichon et al., "Increased activity of coagulation factor XII (Hageman factor) causes hereditary angioedema type III." Am. J. Hum. Genet. (2006) 79: 1098-1104.
Gigli et al., "Interaction of plasma kallikrein with the C1 inhibitor." J. Immunol. (1970) 104:574-581.
Han et al., "Increased vascular permeability in C1 inhibitor-deficient mice mediated by the bradykinin type 2 receptor." J. Clin. Invest. (2002) 109: 1057-1063.

(Continued)

*Primary Examiner* — Kimberly Chong
(74) *Attorney, Agent, or Firm* — Knobbe, Martens, Olson & Bear, LLP

(57) ABSTRACT

Disclosed herein are methods for decreasing Factor 12 and treating or preventing thromboembolic conditions in an individual in need thereof. Examples of disease conditions that can be ameliorated with the administration of antisense compounds targeted to Factor 12 include thrombosis, embolism, and thromboembolism, such as, deep vein thrombosis, pulmonary embolism, myocardial infarction, stroke, and mesenteric thrombosis. Methods for inhibiting Factor 12 can also be used as a prophylactic treatment to prevent individuals at risk for thrombosis and embolism.

21 Claims, No Drawings

(56) References Cited

OTHER PUBLICATIONS

Kaplan et al., "Pathways for bradykinin formation and inflammatory disease." J. Allergy Clin. Immunol. (2002) 109(2): 195-209.
Mackenzie et al., "Plasma prekallikrein levels are positively associated with circulating lipid levels and the metabolic syndrome in children." Appl. Physiol. Nutr. Metab. (2010) 35: 518-525.
Zuraw, "Hereditary Angioedema" N. Engl. J. Med. (2008) 359: 1027-36.
International Search Report for application PCT/US2012/041747 dated Dec. 10, 2012.
Adcock et al., "A laboratory approach to the evaluation of hereditary hypercoagulability" Am. J. Clin. Pathol. (1997) 108(4):434-449.
Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Altmann et al., "Second-generation antisense oligonucleoties: structure-activity relationships and the design of improved signal-transduction inhibitors" Biochem. Soc. Trans. (1996) 24: 630-637.
Altmann et al., "Second Generation of Antisense Oligonucleotides: From Nuclease Resistance to Biological Efficacy in Animals" Chimia (1996) 50: 168-176.
Altmann et al., "Second Generation Antisense Oligonucleotides—Inhibition of PKC-a and c-RAF Kinase Expression by Chimeric Oligonucleotides Incorporating 5'-Substituted Carbocyclic Nucleosides and 2'-O-Ethylene Glycol Substituted Ribonucleosides" Nucleosides Nucleotides (1997) 16(7-9): 917-926.
Altschul et al., "Basic Local Alignment Search Tool" J. Mol. Biol. (1990) 215: 403-410.
Aulak et al., "Chymotrypsin inhibitory activity of normal C1-inhibitor and a P1 Arg to His mutant: evidence for the presence of overlapping reactive centers." Protein Sci. (1993) 2(5): 727-732.
Bertina et al., "Mutation in blood coagulation factor V associated with resistance to activated protein C." Nature (1994) 369(6475):64-67.
Chan et al., "The inhibition of activated factor XII (hageman factor) by antithrombin III: The effect of other plasma proteinase inhibitors" Biochem. Biophys. Res. Comm. (1977) 74(1): 150-158.
Bjork et al., "Mechanism of the anticoagulant action of heparin." Mol Cell Biochem. (1982) 48(3): 161-182.
Citarella et al., "The Second Exon-Encoded Factor XII Region is Involved in the Interaction of Factor XII With Factor XI and Does Not Contribute to the Binding Site for Negatively Charged Surfaces" Blood (1998) 92: 4198-4206.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Citarella et al., "Identification of a putative binding site for negatively charged surfaces in the fibronectin type II domain of human factor XII—an immunochemical and homology modeling approach." Thromb. Haemost. (2000) 84(6): 1057-1065.
Crooke et al., "Basic Principles of Antisense Therapeutics" Antisense Research and Application (1998) Chapter 1:1-50.
Drake et al., "Selective cellular expression of tissue factor in human tissues. Implications for disorders of hemostasis and thrombosis." Am J Pathol (1989) 134(5):1087-1097.
Elayadi et al., "Applications of PNA and LNA oligomers to chemotherapy" Curr. Opinion Invest. Drugs (2001) 2:558-561.
Esnouf et al., "A monoclonal antibody raised against human beta-factor XIIa which also recognizes alpha-factor XIIa but not factor XII or complexes of factor XIIa with C1 esterase inhibitor." Thromb. Haemost. (2000) 83(6): 874-881.
Farsetti et al., "Orphan receptor hepatocyte nuclear factor-4 antagonizes estrogen receptor alpha-mediated induction of human coagulation factor XII gene." Endocrinology (1998) 139(11): 4581-4589.
Foster et al., "Inhibition of the activation of Hageman factor (factor XII) and of platelet aggregation by extracts of Brugia malayi microfilariae." J. Lab. Clin. Med. (1991) 117(5): 344-352.
Foster et al., "Inhibition of the activation of Hageman factor (factor XII) by extracts of Schistosoma mansoni." J. Lab. Clin. Med. (1992) 120(5): 735-9.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-NA" Nucleic Acids Research (2003) 31(21):6365-6372.
Gautschi et al., "Activity of a Novel bcl-2/bcl-xL-Bispecific Antisense Oligonucleotide Against Tumors of Diverse Histologic Origins" J. Natl. Cancer Inst. (2001) 93(6):463-471.
Hazegh-Azam et al., "The Corn Inhibitor of Activated Hageman Factor: Purification and Properties of Two Recombinant Forms of the Protein" Protein Expr. Purif. (1998) 13(2): 143-149.
Hojima et al., "Pumpkin seed inhibitor of human factor XIIa (activated Hageman factor) and bovine trypsin" Biochemistry (1982) 21(16): 3741-3746.
Isawa et al., "Identification and characterization of plasma kallikrein-kinin system inhibitors from salivary glands of the blood-sucking insect Triatoma infestans." FEBS J. (2007) 274(16): 4271-4286.
Kato et al., "Identification and characterization of the plasma kallikrein-kinin system inhibitor, haemaphysalin, from hard tick, Haemaphysalis longicornis" Thromb. Haemost. (2005) 93: 359-67.
Kleinschnitz et al., "Targeting coagulation factor XII provides protection from pathological thrombosis in cerebral ischemia without interfering with hemostasis" J. Exper. Med. (2006) 203:513-518.
Koshkin et al., "LNA (Locked Nucleic Acids): Synthesis of the Adenine, Cytosine, Guanine, 5-Methylcytosine, Thymine and Uracil Biocyclonucleoside Monomers, Oligomerisation, and Unprecedented Nucleic Acid Recognition" Tetrahedron (1998) 54:3607-3630.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Leumann, "DNA Analogues: From Supramolecular Principles to Biological Properties" Bioorganic & Medicinal Chemistry (2002) 10:841-854.
Mahdi et al., "Factor XII interacts with the multiprotein assembly of urokinase plasminogen activator receptor, gC1qR, and cytokeratin 1 on endothelial cell membranes" Blood (2002) 99(10): 3585-3596.
Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.
Martin, "Ein neuer Zugang zu 2'-O-Alkylribonucleosiden and Eigenschaften eren Oligonucleotide" Helv. Chim. Acta (1995) 78: 486-504.
New England Biolabs 1998/99 Catalog (cover page and pp. 121 and 284).
Nielsen, "Corn trypsin inhibitor decreases tissue-type plasminogen activator-mediated fibrinolysis of human plasma." Blood Coagul. Fibronolysis. (2009) 20(3): 191-196.
Nishikawa et al., "Effect of neurotropin® on the activation of the plasma kallikrein-kinin system" Biochem. Pharmacol. (1992) 43(6): 1361-1369.
Niwano et al., "Inhibitory action of amyloid precursor protein against human Hageman factor (factor XII)." J. Lab. Clin. Med. (1995) 125(2): 251-256.
Orum et al., "Locked nucleic acids: A promising molecular family for gene-function analysis and antisense drug development" Curr. Opinion Mol. Ther. (2001) 3(3):239-243.
Rajapakse et al., "A novel anticoagulant purified from fish protein hydrolysate inhibits factor XIIa and platelet aggregation." Life Sci. (2005) 76(22): 2607-2619.
Ratnoff et al., "Inhibition of the activation of hageman factor (factor XII) by eosinophils and eosinophilic constituents" Am. J. Hematol. (1993) 42(1): 138-145.
Reynolds et al., "Rational siRNA design for RNA interference" Nature Biotechnology (2004) 22(3):326-330.

(56) References Cited

OTHER PUBLICATIONS

Ryder et al., "The effect of chemical modification of basic amino acid residues on the activation and amidolytic activity of Hageman factor (factor XII)." J. Lab. Clin. Med. (1993) 122(6): 697-702.

Sampaio et al., "Plant serine proteinase inhibitors. Structure and biochemical applications on plasma kallikrein and related enzymes." Immunopharmacology (1996) 32(1-3): 62-66.

Sanghvi et al., "Heterocyclic Base Modifications in Nucleic Acids and Their Applications in Antisense Oligonucleotides" Antisense Research and Applications (1993) pp. 273-288.

Schousboe et al., "Synchronized inhibition of the phospholipid mediated autoactivation of factor XII in plasma by beta 2-glycoprotein I and anti-beta 2-glycoprotein I." Thromb. Haemost (1995) 73(5): 798-804.

Schwartz et al., "Tissue factor pathway inhibitor endocytosis." Trends Cardiovasc Med. (1997) 7(7):234-239.

Scott et al., "Alpha-1-antitrypsin-Pittsburgh. A potent inhibitor of human plasma factor XIa, kallikrein, and factor XIIf." J. Clin. Invest. (1986) 77(2): 631-634.

Singh et al., "LNA (locked nucleic acids): synthesis and high-affinity nucleic acid recognition" Chem. Commun. (1998) 4:455-456.

Singh et al., "Synthesis of 2'-Amino-LNA: A Novel Conformationally Restricted High-Affinity Oligonucleotide Analogue with a Handle" J. Org. Chem. (1998) 63:10035-10039.

Srivastava et al., "Five- and Six-Membered Conformationally Locked 2',4'-Carbocyclic ribo-Thymidines: Synthesis, Structure, and Biochemical Studies" J. Am. Che,. Soc. (2007) 129:8362-8379.

Tanabe et al., "Isolation and Characterization of Streptoverticillium Anticoagulant (SAC), a Novel Protein Inhibitor of Blood Coagulation Produced by *Streptoverticillium cinnamoneum* subsp. Cinnamoneum" J. Biochem. (1994) 115(4): 743-751.

Wahlestedt et al., "Potent and nontoxic antisense oligonucleoties containing locked nucleic acids" PNAS (2000) 97(10):5633-5638.

Woolf et al., "Specificity of antisense oligonucleotides in vivo" PNAS (1992) 89:7305-7309.

Zhang e al., "PowerBLAST: A New Network BLAST Application for Interactive or Automate Sequence Analysis and Annoation", Genome Res. (1997) 7: 649-656.

Zhou et al., "Fine Tuning of Electrostatics around the Internucleoside Phosphate through Incorporation of Modified 2',4'-Carbocylic-LNAs and -ENAs Leads to Significant Modulation of Antisense Properties" J. Org. Chem. (2009) 74: 118-134.

International Search Report for application PCT/US11/59804 dated May 14, 2012.

Cugno et al., "C1-inhibitor deficiency and angioedema: molecular mechanisms and clinical progress" Trends. Mol. Med. (2009) 15(2): 69-78.

Yau et al., "Selective depletion of factor XI or factor XII with antisense oligonucleotides attenuates catheter thrombosis in rabbits" Blood (2014) 123(13):2102-2107.

\* cited by examiner

SEQUENCE LISTING

```
<160> NUMBER OF SEQ ID NOS: 19

<210> SEQ ID NO 1
<211> LENGTH: 2060
<212> TYPE: DNA
<213> ORGANISM: H. sapiens

<400> SEQUENCE: 1
ctattgatct ggactcctgg ataggcagct ggaccaacgg acggatgcca tgagggctct     60
gctgctcctg gggttcctgc tggtgagctt ggagtcaaca ctttcgattc caccttggga    120
```

| | |
|---|---|
| agcccccaag gagcataagt acaaagctga agagcacaca gtcgttctca ctgtcaccgg | 180 |
| ggagccctgc cacttcccct tccagtacca ccggcagctg taccacaaat gtacccacaa | 240 |
| gggccggcca ggccctcagc cctggtgtgc taccaccccc aactttgatc aggaccagcg | 300 |
| atggggatac tgtttggagc ccaagaaagt gaaagaccac tgcagcaaac acagcccctg | 360 |
| ccagaaagga gggacctgtg tgaacatgcc aagcggcccc cactgtctct gtccacaaca | 420 |
| cctcactgga aaccactgcc agaaagagaa gtgctttgag cctcagcttc tccggttttt | 480 |
| ccacaagaat gagatatggt atagaactga gcaagcagct gtggccagat gccagtgcaa | 540 |
| gggtcctgat gcccactgcc agcggctggc cagccaggcc tgccgcacca acccgtgcct | 600 |
| ccatggggt cgctgcctag aggtggaggg ccaccgcctg tgccactgcc cggtgggcta | 660 |
| caccggagcc ttctgcgacg tggacaccaa ggcaagctgc tatgatggcc gcgggctcag | 720 |
| ctaccgcggc ctggccagga ccacgctctc gggtgcgccc tgtcagccgt gggcctcgga | 780 |
| ggccacctac cggaacgtga ctgccgagca agcgcggaac tggggactgg gcggccacgc | 840 |
| cttctgccgg aacccggaca cgacatccg cccgtggtgt tcgtgctga accgcgaccg | 900 |
| gctgagctgg gagtactgcg acctggcaca gtgccagacc ccaacccagg cggcgcctcc | 960 |
| gacccccgtg tcccctaggc ttcatgtccc actcatgccc cgcagccgg caccgccgaa | 1020 |
| gcctcagccc acgacccgga ccccgcctca gtcccagacc cgggagcct gccggcgaa | 1080 |
| gcgggagcag ccgccttccc tgaccaggaa cggcccactg agctgcgggc agcggctccg | 1140 |
| caagagtctg tcttcgatga cccgcgtcgt tggcgggctg gtggcgctac gcggggcgca | 1200 |
| cccctacatc gccgcgctgt actggggcca cagtttctgc gccggcagcc tcatcgcccc | 1260 |
| ctgctgggtg ctgacggccg ctcactgcct gcaggaccgg cccgcacccg aggatctgac | 1320 |
| ggtggtgctc ggccaggaac gccgtaacca cagctgtgag ccgtgccaga cgttggccgt | 1380 |
| gcgctcctac cgcttgcacg aggccttctc gcccgtcagc taccagcacg acctggctct | 1440 |
| gttgcgccctt caggaggatg cggacggcag ctgcgcgctc ctgtcgcctt acgttcagcc | 1500 |
| ggtgtgcctg ccaagcggcg ccgcgcgacc ctccgagacc acgctctgcc aggtggccgg | 1560 |
| ctggggccac cagttcgagg gggcggagga atatgccagc ttcctgcagg aggcgcaggt | 1620 |
| accgttcctc tccctggagc gctgctcagc cccggacgtg cacggatcct ccatcctccc | 1680 |
| cggcatgctc tgcgcagggt tcctcgaggg cggcaccgat gcgtgccagg tgattccgg | 1740 |
| aggcccgctg gtgtgtgagg accaagctgc agagcgccgg ctcacccctgc aaggcatcat | 1800 |
| cagctgggga tcgggctgtg gtgaccgcaa caagccaggc gtctacaccg atgtggccta | 1860 |
| ctacctggcc tggatccggg agcacaccgt ttcctgattg ctcagggact catctttccc | 1920 |
| tccttggtga ttccgcagtg agagagtggc tggggcatgg aaggcaagat tgtgtcccat | 1980 |
| tcccccagtg cggccagctc cgcgccagga tggcgcagga actcaataaa gtgctttgaa | 2040 |
| aatgctgaga aaaaaaaaaa | 2060 |

<210> SEQ ID NO 2
<211> LENGTH: 1961
<212> TYPE: DNA
<213> ORGANISM: Mus musculus

<400> SEQUENCE: 2

| | |
|---|---|
| tcctgggcag gcagcggggc catcggcaga cgccatgacg gctctgttgt tcctggggtc | 60 |
| tctgctgatg agtctggatc tgacactttc ggctccacca tggaaagact ccaagaaatt | 120 |
| taaggacgca cctgatgggc ccacagtggt tctcactgtg gatgggaggc tctgccattt | 180 |

```
tcccttttcag taccaccgtc agctacacca caaatgcatc cacaaaaggc ggccaggctc      240
ccgcccctgg tgtgctacca cccccaactt tgatgaagat cagcaatggg gatactgctt      300
ggagcccaag aaagtgaaag accattgcag caaacacaac ccgtgccaca aggagggac       360 atgtatcaac accccaatg gccacactg tctctgccct gaacacctca ctgggaaaca       420
ttgccagaaa gagaaatgct ttgagcctca gcttctcaag ttcttccacg agaatgagct      480
atggtttaga acggggccag gaggtgtggc caggtgcgag tgcaaaggtt ctgaggctca      540
ctgcaagccg gtggccagcc aggcctgcag catcaatccg tgccttaatg ggggcagctg      600
cctcctcgtg gaggaccacc cactgtgccg ttgccctaca ggctacactg gatattttg      660 cgacttggac cctttgggcga cctgctatga aggcagggg ctcagctacc ggggccaggc      720
tggaactacg caatcgggtg cgccatgtca gcggtggacc gtggaggcca cctaccggaa      780
catgactgag aagcaagcgc taagctgggg cctgggccac cacgcatttt gccggaaccc      840
agataatgac acacgtccat ggtgcttcgt ctggagtggc gacaggctga gctgggacta      900
ttgcggcctg gagcagtgcc agacgccaac gtttgcacct ctagttgtcc ctgagagtca      960
ggaggagtcc ccgtcccagg caccatctct gtcccatgca ccaaatgact cgaccgatca     1020
tcagacttct ctgtccaaga ccaacacgat gggctgcgga cagaggttcc gcaagggact     1080
gtcctcgttc atgcgcgtgg tgggcggact agtggctctg cctgggtcgc acccctacat     1140
cgctgcactg tactggggta caacttctg cgcgggcagt ctcatcgccc cctgttgggt      1200
gctgaccgcg gctcactgcc tgcagaatcg gccagcgccc gaggaactga cagtggtact     1260
tggtcaagat cgccacaacc agagctgcga gtggtgccag actctggctg tgcgctccta     1320
ccgccttcac gagggcttct cctccatcac ctaccagcac gacttggctc tgctgcgcct     1380
gcaggaaagc aaaaccaaca gttgcgcgat cctgtcacct cacgttcagc ctgtgtgtct     1440
acccagcggc gcggccccac cctctgagac agtgctctgc gaggtggccg gctgggtca      1500 ccagttcgag ggggctgaag aatactccac cttcctgcag gaggcacagg ttccctttat     1560
cgccctggat cgctgctcca actctaacgt gcacggagac gccattctcc ctgggatgct     1620
ttgcgctggc ttcttggagg gaggcaccga tgcctgccag ggtgactccg ggggccctct     1680
ggtgtgtgag gaaggaactg cagaacatca gctcaccctg cgcggagtca tcagctgggg     1740
ctccggctgt ggtgaccgca acaagcccgg agtctacaca gacgtggcca actacctggc     1800
ttggatccag aagcatattg cttcataact aaccaggctt tatccttccc tccttgtgtg     1860
ctccttggga tgggacgatg aatgtggcat gctgggtcac agtgaagcta gtgccccgac     1920
actgggggca cagaaactca ataaagtgct ttgaaaacgt t                         1961
```

<210> SEQ ID NO 3  
<211> LENGTH: 2128  
<212> TYPE: DNA  
<213> ORGANISM: Rattus norvegicus

<400> SEQUENCE: 3

```
caggaaccca tctcggtact ctgcttccac cagccttgcc ctgctcacga gggttcgacg       60
gcgctgttct tctgggcttt ctgtgaagtc tgtgctcctc aggcccagga gggagcttaa      120
ccaatctcca cctctgaggt ttctgagacc tttgcccaca tctattgatc cttactctgg      180
ggcaggcagc tgggccattg gcggacgcca tgacggctct gttgttcctg gggtctctgc      240
tgatgagtct ggacttgaca ctttcggcgc caccgtggaa gtccaaggag ttcaaggacg      300
```

```
gagctggcga tccctctgtg gttctcactg tggacgggaa gctctgccac tttcccttc      360
agtaccaccg tcgcctgtac cacaaatgca tccacaaagg acagccaggc tccaggccct      420
ggtgtgctac cacccccaac tttgacgagg accagcaatg gggatactgc ttggagccca      480
agaaagtgaa agaccattgc agcaaacaca gcccctgcca caaggagggg acgtgtgtca      540
acaccccaa cggcccgcac tgtctctgcc ctgaacacct caccgggaaa cattgccaga       600
gagagaaatg ctttgagtct cagctcctca agttcttcca tgagaatgag atatggttta     660
gaactgggcc aggaggtgtg gccaggtgcc agtgcaaagg tcctcaggct gtttgcaagc      720
tgctgaccag tcaggtttgc agggtcaatc cgtgccttaa tggaggcacc tgcctcctcg      780
tggaggacca ccgactgtgc cactgccctg caggctatgc cggacctttt tgcgacttag      840
accttaaggc gacttgctac gaagacaggg gtctcagcta ccggggccag gctaaaacta      900
ctctgtcggg tgcaccatgt cagcggtggg cctcggaggc cacctaccgg aacatgactg      960
agacgcaagc tctaagctgg ggcctgggcc accacgcatt ctgccggaac ccagataatg     1020
acacacgtcc atggtgctac gtctggagtg gcgacaggct gagctgggac tactgcgacc     1080
tggaacagtg ccagatgcca acgctcacat ctccggtttc ccctgagagt cacgacatgc     1140
tgaagccccg gcctcccata ttgcagatgc ctcagttccc gtctctgtcc gatgcactag     1200
acaactcgac ccgtaatcag aatgttgtgt ccaggaccag tacggtggtc tgcggacaga     1260
ggttcgcaa gcgactgtcc tcgctcaggc gcgtggtggg cggactagtg gctctgcctg      1320
gatcgcatcc ctacatcgct gcactgtact ggggcgacag cttctgcgca ggcagtctca     1380
tcgacccctg ctgggtgctg accgctgctc actgcttgca gaaacggcca gcgcccgagg     1440
aactgacagt ggtacttggt caagatcgcc ataaccagag ctgcgagagg tgccagactc     1500
tggctgtgca ctcctaccgc cttcacgagg gcttctcttc caaaacctac cagcatgatt     1560
tggctctgct gcgcctgcgg gggaggaaaa acagctgcgc gatcttgtcg cctcatgtcc     1620
agccggtgtg tctgcccagc agcgcggccc caccctctga cagtgctc tgcgaggtgg       1680
ccggctgggg tcatcagttc gagggggctg aagaatacgc cacctttctg caggaggcac     1740
aggtacccct catctccctg gatcgctgct ccagctctaa cgtgcacgga gacgccatcc     1800
tgcctgggat gctttgtgct ggcttcttgg agggaggcgc cgatgcctgt cagggtgact     1860
ccggggggtcc tctggtatgt gatgaaggag ttacagagcg tcagctcacc ctgcgaggag    1920
tcatcagctg gggctccggc tgtggtgacc ggaacaagcc cggggtctac actgacgtgg     1980
ccaattacct ggattggatc caggagcata ctgctttcta agtaaccagg gtcggtcctt     2040
gcgaagctag tggctgggcc ccagggacac agaaactcaa taaagtgctt tgaaaacgtt     2100
aaaaaaaaaa aaaaaaaaaa aaaaaaa                                         2128
```

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
caaaggaggg acatgtatca acac                                             24

<210> SEQ ID NO 5
<211> LENGTH: 20
<212> TYPE: DNA
<213> ORGANISM: Artificial Sequence

```
<220> FEATURE:
<223> OTHER INFORMATION: Primer

<400> SEQUENCE: 5
ctggcaatgt ttcccagtga                                            20

<210> SEQ ID NO 6
<211> LENGTH: 24
<212> TYPE: DNA
<213> ORGANISM: Artificial Sequence
<220> FEATURE:
<223> OTHER INFORMATION: Probe

<400> SEQUENCE: 6
cccaatgggc cacactgtct ctgc                                       24

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gcatgggaca gagatggtgc                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gcacacaagg agggaaggat                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cgtcccatcc caaggagcac                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
gtgacccagc atgccacatt                                            20

<210> SEQ ID NO 11
<211> LENGTH: 17
<212> TYPE: DNA
<213> ORGANISM: Artificial Sequence
<220> FEATURE:
<223> OTHER INFORMATION: Primer

<400> SEQUENCE: 11
gggccaccac gcattct                                               17
```

```
<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
cgccactcca gacgtagca                                                19

<210> SEQ ID NO 13
<211> LENGTH: 27
<212> TYPE: DNA
<213> ORGANISM: Artificial Sequence
<220> FEATURE:
<223> OTHER INFORMATION: Probe

<400> SEQUENCE: 13
ccggaaccca gataatgaca cacgtcc                                       27

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
ggcaatgttt cccggtgagg                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
cgccttaagg tctaagtcgc                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
cgtcagtgta gaccccgggc                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
cccggtgagg tgttcagggc                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 18
tcgcaaggac cgaccctggt                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
ggcccagcca ctagcttcgc                                              20
```

METHODS FOR MODULATING FACTOR 12 EXPRESSION

CROSS REFERENCED TO RELATED APPLICATIONS

This application is a U.S. National Phase filing under 35 U.S.C. §371 claiming priority to International Serial No. PCT/US2011/059804 filed Nov. 8, 2011, which claims priority to U.S. Provisional Application 61/411,309, filed Nov. 8, 2010, each of which is incorporated herein by reference in its entirety.

SEQUENCE LISTING

The present application is being filed along with a Sequence Listing in electronic format. The Sequence Listing is provided as a file entitled BIOL0138USASEQ.txt created May 8, 2013, which is 11 Kb in size. The information in the electronic format of the sequence listing is incorporated herein by reference in its entirety.

FIELD OF THE INVENTION

Embodiments of the present invention provide methods for reducing expression of Factor 12 mRNA and protein in an animal. Such methods are useful to treat, prevent, or ameliorate thromboembolic conditions.

BACKGROUND OF THE INVENTION

The circulatory system requires mechanisms that prevent blood loss, as well as those that counteract inappropriate intravascular obstructions. Generally, coagulation comprises a cascade of reactions culminating in the conversion of soluble fibrinogen to an insoluble fibrin gel. The steps of the cascade involve the conversion of an inactive zymogen to an activated enzyme. The active enzyme then catalyzes the next step in the cascade.

Coagulation Cascade

The coagulation cascade may be initiated through two branches, the tissue factor pathway (also "extrinsic pathway"), which is the primary pathway, and the contact activation pathway (also "intrinsic pathway").

The tissue factor pathway is initiated by the cell surface receptor tissue factor (TF, also referred to as factor III), which is expressed constitutively by extravascular cells (pericytes, cardiomyocytes, smooth muscle cells, and keratinocytes) and expressed by vascular monocytes and endothelial cells upon induction by inflammatory cytokines or endotoxin. (Drake et al., *Am J Pathol* 1989, 134:1087-1097). TF is the high affinity cellular receptor for coagulation factor VIIa, a serine protease. In the absence of TF, VIIa has very low catalytic activity, and binding to TF is necessary to render VIIa functional through an allosteric mechanism. (Drake et al., *Am J Pathol* 1989, 134:1087-1097). The TF-VIIa complex activates factor X to Xa. Xa in turn associates with its co-factor factor Va into a prothrombinase complex which in turn activates prothrombin, (also known as factor II or factor 2) to thrombin (also known as factor IIa, or factor 2a). Thrombin activates platelets, converts fibrinogen to fibrin and promotes fibrin crosslinking by activating factor XIII, thus forming a stable plug at sites where TF is exposed on extravascular cells. In addition, thrombin reinforces the coagulation cascade response by activating factors V and VIII.

The contact activation pathway is triggered by activation of factor XII (also factor 12) to XIIa (also factor 12a). Factor XIIa converts XI to XIa, and XIa converts IX to IXa. IXa associates with its cofactor VIIIa to convert X to Xa. The two pathways converge at this point as factor Xa associates factor Va to activate prothrombin (factor II) to thrombin (factor IIa).

Inhibition of Coagulation

At least three mechanisms keep the coagulation cascade in check, namely the action of activated protein C, antithrombin, and tissue factor pathway inhibitor. Activated protein C is a serine protease that degrades cofactors Va and VIIIa. Protein C is activated by thrombin with thrombomodulin, and requires coenzyme Protein S to function. Antithrombin is a serine protease inhibitor (serpin) that inhibits serine proteases: thrombin, Xa, XIIa, XIa and IXa. Tissue factor pathway inhibitor inhibits the action of Xa and the TF-VIIa complex. (Schwartz A L et al., *Trends Cardiovasc Med.* 1997; 7:234-239.)

Disease

Thrombosis is the pathological development of blood clots, and an embolism occurs when a blood clot migrates to another part of the body and interferes with organ function. Thromboembolism may cause conditions such as deep vein thrombosis, pulmonary embolism, myocardial infarction, and stroke. Significantly, thromboembolism is a major cause of morbidity affecting over 2 million Americans every year. (Adcock et al. *American Journal of Clinical Pathology.* 1997; 108:434-49). While most cases of thrombosis are due to acquired extrinsic problems, for example, surgery, cancer, immobility, some cases are due to a genetic predisposition, for example, antiphospholipid syndrome and the autosomal dominant condition, Factor V Leiden. (Bettina R M et al. *Nature* 1994; 369:64-67.)

Treatment

The most commonly used anticoagulants, warfarin, heparin, and low molecular weight heparin (LMWH), all possess significant drawbacks.

Warfarin is typically used to treat patients suffering from atrial fibrillation. The drug interacts with vitamin K-dependent coagulation factors which include factors II, VII, IX and X. Anticoagulant proteins C and S are also inhibited by warfarin. Drug therapy using warfarin is further complicated by the fact that warfarin interacts with other medications, including drugs used to treat atrial fibrillation, such as amiodarone. Because therapy with warfarin is difficult to predict, patients must be carefully monitored in order to detect any signs of anomalous bleeding.

Heparin functions by activating antithrombin which inhibits both thrombin and factor X. (Bjork I, Lindahl U. *Mol Cell Biochem.* 1982 48: 161-182.) Treatment with heparin may cause an immunological reaction that makes platelets aggregate within blood vessels that can lead to thrombosis. This side effect is known as heparin-induced thrombocytopenia (HIT) and requires patient monitoring. Prolonged treatment with heparin may also lead to osteoporosis. LMWH can also inhibit Factor 2, but to a lesser degree than unfractioned heparin (UFH). LMWH has been implicated in the development of HIT.

Thus, current anticoagulant agents lack predictability and specificity and, therefore, require careful patient monitoring to prevent adverse side effects, such as bleeding complications. There are currently no anticoagulants which target only the intrinsic or extrinsic pathway.

SUMMARY OF THE INVENTION

Provided herein are methods for modulating expression of Factor 12 mRNA and protein. In certain embodiments, Factor 12 specific inhibitors modulate expression of Factor 12 mRNA and protein. In certain embodiments, Factor 12 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, Factor 12 mRNA levels are reduced. In certain embodiments, Factor 12 protein levels are reduced. In certain embodiments, Factor 12 mRNA and protein levels are reduced. Such reduction can occur in a time-dependent manner or in a dose-dependent manner.

Also provided are methods useful for preventing, treating, and ameliorating diseases, disorders, and conditions. In certain embodiments, such diseases, disorders, and conditions are thromboembolic conditions. Such thromboembolic conditions include the categories of thrombosis, embolism, and thromboembolism. In certain embodiments such thromboembolic conditions include deep vein thrombosis, pulmonary embolism, myocardial infarction, stroke, and mesenteric thrombosis.

Such diseases, disorders, and conditions can have one or more risk factors, causes, or outcomes in common. Certain risk factors and causes for development of a thromboembolic condition include immobility, surgery (particularly orthopedic surgery), malignancy, pregnancy, older age, use of oral contraceptives, atrial fibrillation, previous thromboembolic condition, chronic inflammatory disease, and inherited or acquired prothrombotic clotting disorders. Certain outcomes associated with development of a thromboembolic condition include decreased blood flow through an affected vessel, death of tissue, and death.

In certain embodiments, methods of treatment include administering a Factor 12 specific inhibitor to an individual in need thereof. In certain embodiments, the Factor 12 specific inhibitor is a nucleic acid. In certain embodiments, the nucleic acid is an antisense compound. In certain embodiments, the antisense compound is a modified oligonucleotide.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

DEFINITIONS

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to Factor 12 is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" or "ameliorate" or "amerliorating" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antidote compound" refers to a compound capable of decreasing the intensity or duration of any antisense-mediated activity.

"Antidote oligonucleotide" means an antidote compound comprising an oligonucleotide that is complementary to and capable of hybridizing with an antisense compound.

"Antidote protein" means an antidote compound comprising a peptide.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Coagulation factor" means any of factors I, II, III, IV, V, VII, VIII, IX, X, XI, XII, XIII, or TAFI in the blood coagulation cascade. "Coagulation factor nucleic acid" means any nucleic acid encoding a coagulation factor. For example, in certain embodiments, a coagulation factor nucleic acid includes, without limitation, a DNA sequence encoding a coagulation factor (including genomic DNA comprising introns and exons), an RNA sequence transcribed from DNA encoding a coagulation factor, and an mRNA sequence encoding a coagulation factor. "Coagulation factor mRNA" means an mRNA encoding a coagulation factor protein.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Factor 12 nucleic acid" or "Factor XII nucleic acid" or "F 12 nucleic acid" or "F XII nucleic acid" means any nucleic acid encoding Factor 12. For example, in certain embodiments, a Factor 12 nucleic acid includes a DNA sequence encoding Factor 12, an RNA sequence transcribed from DNA encoding Factor 12 (including genomic DNA comprising introns and exons), and an mRNA sequence encoding Factor 12. "Factor 12 mRNA" means an mRNA encoding a Factor 12 protein.

"Factor 12 specific inhibitor" refers to any agent capable of specifically inhibiting the expression of Factor 12 mRNA and/or Factor 12 protein at the molecular level. For example, Factor 12 specific inhibitors include nucleic acids (including antisense compounds), peptides, antibodies, small molecules, and other agents capable of inhibiting the expression of Factor 12 mRNA and/or Factor 12 protein. In certain embodiments, by specifically modulating Factor 12 mRNA expression and/or Factor 12 protein expression, Factor 12 specific inhibitors may affect other components of the coagulation cascade including downstream components. Similarly, in certain embodiments, Factor 12 specific inhibitors may affect other molecular processes in an animal.

"Factor 12 specific inhibitor antidote" means a compound capable of decreasing the effect of a Factor 12 specific inhibitor. In certain embodiments, a Factor 12 specific inhibitor antidote is selected from a Factor 12 peptide; a Factor 12 antidote oligonucleotide, including a Factor 12 antidote compound complementary to a Factor 12 antisense compound; and any compound or protein that affects the intrinsic or extrinsic coagulation pathway.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for thromboembolic conditions" means identifying an animal having been diagnosed with a thromboembolic condition or identifying an animal predisposed to develop a thromboembolic condition. Individuals predisposed to develop a thromboembolic condition include those having one or more risk factors for thromboembolic conditions including immobility, surgery (particularly orthopedic surgery), malignancy, pregnancy, older age, use of oral contraceptives, and inherited or acquired prothrombotic clotting disorders. Such identification may be accomplished by any method including evaluating an individual's medical history and standard clinical tests or assessments.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment.

"3' target site" refers to the 3'-most nucleotide of a target segment.

"Therapeutically effective amount" means an amount of a pharmaceutical agent that provides a therapeutic benefit to an individual.

"Thromboembolic condition" means any disease, disorder, or condition involving an embolism caused by a thrombus. Examples of such diseases, disorders, and conditions include the categories of thrombosis, embolism, and thromboembolism. In certain embodiments, such disease disorders, and conditions include deep vein thrombosis, pulmonary embolism, myocardial infarction, stroke, and mesenteric thrombosis.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Embodiments of the present invention provide methods for decreasing Factor 12 mRNA and protein expression.

Embodiments of the present invention provide methods for the treatment, prevention, or amelioration of diseases, disorders, and conditions associated with Factor 12 in an individual in need thereof. Also contemplated are methods for the preparation of a medicament for the treatment, prevention, or amelioration of a disease, disorder, or condition associated with Factor 12. Factor 12 associated diseases, disorders, and conditions include thromboembolic conditions such as thrombosis, embolism, thromboembolism, deep vein thrombosis, pulmonary embolism, myocardial infarction, stroke, mesenteric thrombosis.

Embodiments of the present invention provide for the use of a Factor 12 specific inhibitor for treating, preventing, or ameliorating a Factor 12 associated disease. In certain embodiments, Factor 12 specific inhibitors are nucleic acids (including antisense compounds), peptides, antibodies, small molecules, and other agents capable of inhibiting the expression of Factor 12 mRNA and/or Factor 12 protein.

In certain embodiments of the present invention, Factor 12 specific inhibitors are peptides or proteins, such as, but not limited to, yellowfin sole anticoagulant protein (YAP) as described in *Life Sci.* 2005. 76: 2607-19; corn inhibitor of activated Hageman factor (CHFI) as described in *Protein Expr. Purif.* 1998. 13: 143-9; corn trypsin inhibitor as described in *Blood Coagul. Fibronolysis.* 2009. 20: 191-6; triafestin-1 and triafestin-2 as described in FEBS J. 2007. 274: 4271-86; YHK9 and vitronectin as described in *Blood.* 2002. 99: 3585-96; torresea cearensis trypsin inhibitor as described in *Immunopharmacology.* 1996. 32: 62-6; amyloid precursor protein as described in *J. Lab. Clin. Med.* 1995. 125: 251-6; streptoverticillium anticoagulant I as described in *J. Biochem.* 1994. 115: 743-51; C1-inhibitor as described in *Protein Sci.* 1993. 2: 727-32; antithrombin III as described in *Biochem. Biophys. Res. Comm.* 1977. 74: 150-8; and alpha-1-antitrypsin-Pittsburgh as described in *J. Clin. Invest.* 1986. 77: 631-4.

In certain embodiments of the present invention, Factor 12 specific inhibitors are antibodies, such as, but not limited to, KOK5 antibody as described in *Thromb. Haemost.* 2000. 84: 1057-65; mAb 2/215 as described in *Thromb. Haemost.* 2000. 83: 874-81; B7C9 as described in *Blood.* 1998. 92: 4198-206; beta 2-glycoprotein I and anti-beta 2-glycoprotein I as described in *Thromb. Haemost.* 1995. 73: 798-804; and mAb 2/215 and mAb 201/9 as described in USPPN 2009/0304685.

In certain embodiments of the present invention, Factor 12 specific inhibitors are small molecules, such as, but not limited to, neurotropin as described in *Biochem. Pharmacol.* 1992. 43: 1361-9; haemaphysalin as described in *Thromb. Haemost.* 93: 359-67; transcription factor hepatocyte nuclear factor-4 as described in *Endocrinology.* 1998. 139: 4581-9; phenylglyoxal hydrate as described in *J. Lab. Clin. Med.* 1993. 122: 697-702; eosinophilic extracts as described in *Am. J. Hematol.* 1993. 42: 138-45; schistosome extracts as described in *J. Lab. Clin. Med.* 1992. 120: 735-9; extracts of *Brugia malayi* microfilariae as described in *J. Lab. Clin. Med.* 1991. 117: 344-52; H-D-Pro-Phe-Arg-chloromethylketone as described in USPPN US 2010/0119512; and *Curcurbita maxima* iso inhibitor as described in *Biochemistry.* 1982. 21: 3741-3746.

Embodiments of the present invention provide for methods of treating, preventing, or ameliorating a thromboembolic condition in an animal, comprising administering to the animal a therapeutically effective amount of a Factor 12 specific inhibitor, wherein the thromboembolic condition is ameliorated in the animal.

In certain embodiments, the animal is a human.

In certain embodiments, the thromboembolic condition is any of the group consisting of thrombosis, embolism, thromboembolism, deep vein thrombosis, pulmonary embolism, myocardial infarction, stroke, mesenteric thrombosis.

In certain embodiments, the Factor 12 specific inhibitor is a nucleic acid.

In certain embodiments, the nucleic acid is a modified oligonucleotide.

In certain embodiments, the modified oligonucleotide consists of 12 to 30 linked nucleosides.

In certain embodiments, the modified oligonucleotide is a single-stranded oligonucleotide.

In certain embodiments, the modified oligonucleotide consists of 20 linked nucleosides.

In certain embodiments, the modified oligonucleotide has a nucleobase sequence that is 100% complementary to a human Factor 12 nucleic acid.

In certain embodiments, the modified oligonucleotide comprises at least one modified internucleoside linkage. In certain embodiments, each modified internucleoside linkage is a phosphorothioate internucleoside linkage.

In certain embodiments, at least one nucleoside of the modified oligonucleotide comprises a modified sugar. In certain embodiments, the modified sugar is a bicyclic sugar. In certain embodiments, the bicyclic sugar comprises a 4'-CH(CH$_3$)—O-2' bridge.

In certain embodiments, the modified sugar comprises a 2'-O-methoxyethyl group.

In certain embodiments, at least one nucleoside of the modified oligonucleotide comprises a modified nucleobase. In certain embodiments, the modified nucleobase is a 5'-methylcytosine.

In certain embodiments, at least one nucleoside of the modified oligonucleotide comprises at least one tetrahydropyran modified nucleoside wherein a tetrahydropyran ring replaces the furanose ring. In certain embodiments, each of the at least one tetrahydropyran modified nucleoside has the structure:

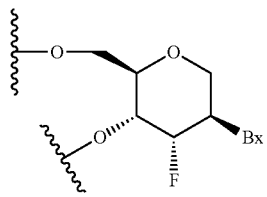

wherein Bx is an optionally protected heterocyclic base moiety.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned immediately adjacent to and between the 5' wing segment and the 3' wing segment and wherein each nucleoside of each wing segment comprises a modified sugar. In some such embodiments, each cytosine in the modified oligonucleotide is a 5-methylcytosine.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

In certain embodiments, the modified oligonucleotide of the compound comprises:
(i) a gap segment consisting of fourteen linked deoxynucleosides;
(ii) a 5' wing segment consisting of three linked nucleosides;
(iii) a 3' wing segment consisting of three linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

In certain embodiments, the modified oligonucleotide of the compound comprises:
(i) a gap segment consisting of thirteen linked deoxynucleosides;
(ii) a 5' wing segment consisting of two linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage. In some such embodiments, each cytosine in the modified oligonucleotide is a 5-methylcytosine.

Embodiments of the present invention provide for methods comprising (1) identifying an animal at risk for a thromboembolic condition; and (2) administering to the at risk animal a therapeutically effective amount of a modified oligonucleotide consisting of 12 to 30 linked nucleosides, wherein the modified oligonucleotide is at least 80% complementary to a Factor 12 nucleic acid.

In certain embodiments, the modified oligonucleotide is at least 90% complementary to a human Factor 12 nucleic acid. In certain embodiments, the modified oligonucleotide is 100% complementary to a human Factor 12 nucleic acid.

In certain embodiments, the administering of a modified oligonucleotide inhibits thrombus and clot formation.

In certain embodiments, the administering of a modified oligonucleotide prolongs aPTT.

In certain embodiments, the administering of a modified oligonucleotide does not prolong PT.

In certain embodiments, the administering of a modified oligonucleotide prolongs aPTT and does not prolong PT.

In certain embodiments, the administering of a modified oligonucleotide decreases Platelet Factor 4 (PF-4).

In certain embodiments, the administering of a modified oligonucleotide increases time for thrombus formation.

In certain embodiments, the administering of the modified oligonucleotide decreases fibrin formation.

In certain embodiments, the administering of a modified oligonucleotide does not increase bleeding in the at risk animal as compared to an animal not administered a modified oligonucleotide.

In certain embodiments, the animal is a human.

In certain embodiments, the Factor 12 nucleic acid is a human Factor 12 nucleic acid.

In certain embodiments, the thromboembolic condition is any of the group consisting of thrombosis, embolism, thromboembolism, deep vein thrombosis, pulmonary embolism, myocardial infarction, stroke, mesenteric thrombosis or a combination thereof.

In certain embodiments, the modified oligonucleotide is co-administered with any of the group selected from aspirin, clopidogrel, dipyridamole, heparin, lepirudin, ticlopidine, warfarin, apixaban, rivaroxaban, and LOVENOX.

In certain embodiments, the modified oligonucleotide is co-administered with an anti-platelet therapy. In certain embodiments, the anti-platelet therapy is any of the group selected from an ADP receptor inhibitor, NSAID, phosphodiesterase inhibitor, glycoprotein IIB/IIIA inhibitor, adenosine reuptake inhibitor, or a combination thereof. In certain embodiments, the NSAID is aspirin, naproxen, or a combination of both.

In certain embodiments, the modified oligonucleotide is concomitantly administered with any of the group selected from aspirin, clopidogrel, dipyridamole, heparin, lepirudin, ticlopidine, warfarin, apixaban, rivaroxaban, and LOVENOX.

In certain embodiments, the modified oligonucleotide is concomitantly administered with an anti-platelet therapy. In certain embodiments, the anti-platelet therapy is any of the group selected from an ADP receptor inhibitor, NSAID, phosphodiesterase inhibitor, glycoprotein IIB/IIIA inhibitor, adenosine reuptake inhibitor, or a combination thereof. In certain embodiments, the NSAID is aspirin, naproxen, or a combination of both.

In certain embodiments, the administering is parenteral administration. In certain embodiments, the parenteral administration is any of subcutaneous or intravenous administration.

Embodiments of the present invention provide the use of Factor 12 specific inhibitors as described herein in the manufacture of a medicament for treating, ameliorating, or preventing a thromboembolic condition such as thrombosis, embolism, thromboembolism, deep vein thrombosis, pulmonary embolism, myocardial infarction, stroke, mesenteric thrombosis.

Embodiments of the present invention provide the use of a Factor 12 specific inhibitor as described herein in the manufacture of a medicament for treating, preventing, or ameliorating a thromboembolic condition as described herein in a patient who is subsequently administered an additional agent or therapy as described herein.

Embodiments of the present invention provide a kit for treating, preventing, or ameliorating a thromboembolic condition as described herein wherein the kit comprises:
(i) a Factor 12 specific inhibitor as described herein; and alternatively
(ii) an additional agent or therapy as described herein.

A kit of the present invention may further include instructions for using the kit to treat, prevent, or ameliorate a thromboembolic condition as described herein by combination therapy as described herein.

In certain embodiments, the invention provides a compound comprising a modified oligonucleotide. In certain embodiments, the compound of the invention comprises a modified oligonucleotide consisting of 12 to 30 linked nucleosides.

In certain embodiments, the modified oligonucleotide targets a Factor 12 nucleic acid. In certain embodiments, the accession number of the Factor 12 nucleic acid includes, but is not limited to, GENBANK Accession No. NM_000505 (incorporated herein as SEQ ID NO: 1), GENBANK Accession No. NM_021489 (incorporated herein as SEQ ID NO: 2), and GENBANK Accession No. NM_001014006 (incorporated herein as SEQ ID NO: 3).

In certain embodiments, the compound of the invention may comprise a modified oligonucleotide comprising a nucleobase sequence at least 80%, at least 85%, at least 90%, at least 95%, at least 96%, at least 97%, at least 98%, or at least 99% complementary to an equal length portion of SEQ ID NO: 1. In certain embodiments, the compound of the invention may comprise a modified oligonucleotide comprising a nucleobase sequence 100% complementary to an equal length portion of SEQ ID NO: 1.

In certain embodiments, the nucleobase sequence of the modified oligonucleotide is 100% complementary to a nucleobase sequence of SEQ ID NO: 1 or SEQ ID NO: 2 or SEQ ID NO: 3.

Embodiments of the present invention provide methods comprising identifying an animal having a clotting disorder by administering to the animal a therapeutically effective amount of a compound comprising a modified oligonucleotide consisting of 12 to 30 linked nucleosides, wherein the modified oligonucleotide is complementary to a Factor 12 nucleic acid.

Embodiments of the present invention provide methods comprising reducing the risk for thromboembolic conditions in an animal by administering to the animal a therapeutically effective amount of a compound comprising a modified oligonucleotide consisting of 12 to 30 linked nucleosides, wherein the modified oligonucleotide is complementary to a Factor 12 nucleic acid.

Embodiments of the present invention provide methods comprising treating a clotting disorder in an animal by administering to the animal a therapeutically effective amount of a compound comprising a modified oligonucleotide consisting of 12 to 30 linked nucleosides, wherein the modified oligonucleotide is complementary to a Factor 12 nucleic acid.

Embodiments of the present invention provide methods comprising inhibiting Factor 12 expression in an animal by administering to the animal a therapeutically effective amount of a compound comprising a modified oligonucleotide consisting of 12 to 30 linked nucleosides, wherein the modified oligonucleotide is complementary to a Factor 12 nucleic acid.

In certain embodiments, the Factor 12 inhibition in the animal is reversed by administering an antidote to the modified oligonucleotide.

In certain embodiments, the antidote is an oligonucleotide complementary to the modified oligonucleotide.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Factor 12 nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a Factor 12 nucleic acid may be shortened or truncated. For example, a single subunit may be deleted from the 5' end (5' truncation), or alternatively from the 3' end (3' truncation). A shortened or truncated antisense compound targeted to a Factor 12 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Factor 12 nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 5-8-5, or 6-8-6.

In certain embodiments, the antisense compound has a "wingmer" motif, having a wing-gap or gap-wing configuration, i.e. an X—Y or Y—Z configuration as described above for the gapmer configuration. Thus, wingmer configurations of the present invention include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a Factor 12 nucleic acid possess a 5-10-5 gapmer motif.

In certain embodiments, antisense compounds targeted to a Factor 12 nucleic acid possess a 3-14-3 gapmer motif.

In certain embodiments, antisense compounds targeted to a Factor 12 nucleic acid possess a 2-13-5 gapmer motif.

In certain embodiments, antisense compounds targeted to a Factor 12 nucleic acid possess a 5-8-5 gapmer motif.

In certain embodiments, antisense compounds targeted to a Factor 12 nucleic acid possess a 6-8-6 gapmer motif.

In certain embodiments, an antisense compound targeted to a Factor 12 nucleic acid has a gap-widened motif.

In certain embodiments, a gap-widened antisense oligonucleotide targeted to a Factor 12 nucleic acid has a gap segment of fourteen 2'-deoxyribonucleotides positioned immediately adjacent to and between wing segments of three chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a Factor 12 nucleic acid has a gap segment of thirteen 2'-deoxyribonucleotides positioned immediately adjacent to and between a 5' wing segment of two chemically modified nucleosides and a 3' wing segment of five chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode Factor 12 include, without limitation, the following: GENBANK Accession No. NM_000505 (incorporated herein as SEQ ID NO: 1), GENBANK Accession No. NM_021489 (incorporated herein as SEQ ID NO: 2), and GENBANK Accession No. NM_001014006 (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Factor 12 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Factor 12 mRNA levels are indicative of inhibition of Factor 12 expression. Reductions in levels of a Factor 12 protein are also indicative of inhibition of target mRNA expression. Further, phenotypic changes are indicative of inhibition of Factor 12 expression. For example, a prolonged aPTT time can be indicative of inhibition of Factor 12 expression. In another example, prolonged aPTT time in conjunction with a normal PT time can be indicative of inhibition of Factor 12 expression. In another example, a decreased quantity of Platelet Factor 4 (PF-4) can be indicative of inhibition of Factor 12 expression. In another example, reduced formation of thrombus or increased time for thrombus formation can be indicative of inhibition of Factor 12 expression.

Hybridization

In some embodiments, hybridization occurs between an antisense compound disclosed herein and a Factor 12 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Factor 12 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Factor 12 nucleic acid).

Non-complementary nucleobases between an antisense compound and a Factor 12 nucleic acid may be tolerated provided that the antisense compound remains able to specifically hybridize to a target nucleic acid. Moreover, an antisense compound may hybridize over one or more segments of a Factor 12 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Factor 12 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a Factor 12 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Factor 12 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Factor 12 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Factor 12 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_1$)—(CH$_2$)$_2$—N(R$_m$)(R$_n$), where each R$_l$, R$_m$, and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'—CH (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N (OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N (R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., Tetrahedron, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $Sh_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research,* 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

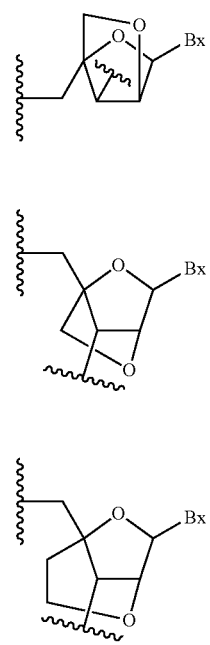

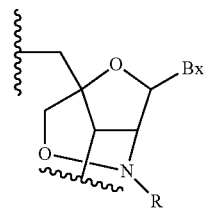

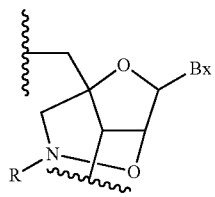

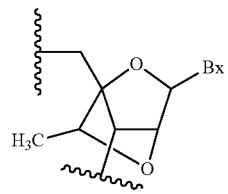

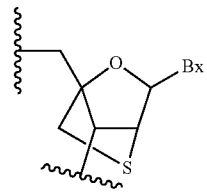

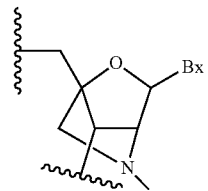

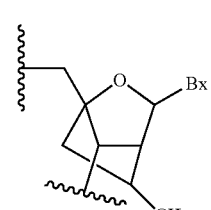

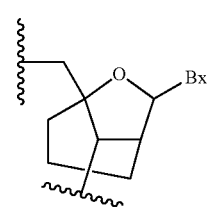

wherein Bx is the base moiety and R is independently H, a protecting group or $C_1$-$C_{12}$ alkyl.

In certain embodiments, bicyclic nucleosides are provided having Formula I:

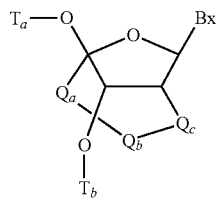

I wherein:
Bx is a heterocyclic base moiety;
-$Q_a$-$Q_b$-$Q_c$- is —$CH_2$—N($R_c$)—$CH_2$—, —C(=O)—N($R_e$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

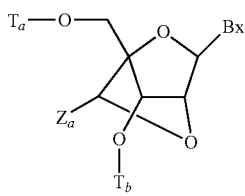

II wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

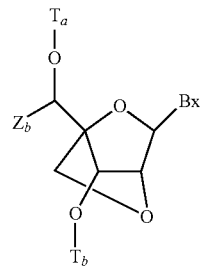

III wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

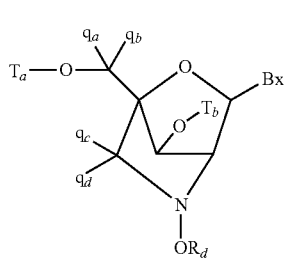

IV wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

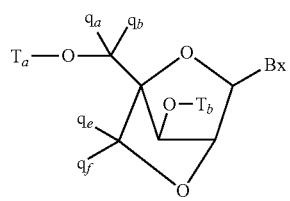

V wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

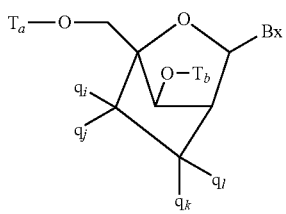

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$F, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F—HNA) or those compounds having Formula VII:

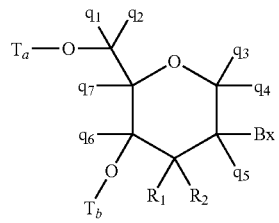

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE.

In certain embodiments, the 2'-MOE modified nucleosides are arranged in a gapmer motif. In certain embodiments, the modified sugar moiety is a bicyclic nucleoside having a (4'-$CH(CH_3)$—O-2') bridging group. In certain embodiments, the (4'-$CH(CH_3)$—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a Factor 12 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a Factor 12 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Factor 12 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a Factor 12 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Factor 12 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of Factor 12 nucleic acids can be assessed by measuring Factor 12 protein levels. Protein levels of Factor 12 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human Factor 12 are commercially available.

In Vivo Testing of Antisense Compounds

Antisense compounds, for example, antisense oligonucleotides, are tested in animals to assess their ability to inhibit expression of Factor 12 and produce phenotypic changes, such as, prolonged aPTT, prolonged aPTT time in conjunction with a normal PT, decreased quantity of Platelet Factor 4 (PF-4), and reduced formation of thrombus or increased time for thrombus formation. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from liver tissue and changes in Factor 12 nucleic acid expression are measured. Changes in Factor 12 protein levels are also measured using a thrombin generation assay. In addition, effects on clot times, e.g. PT and aPTT, are determined using plasma from treated animals.

Tolerability

In certain embodiments, the compounds provided herein display minimal side effects. Side effects include responses to the administration of the antisense compound that are typically unrelated to the targeting of factor 12, such as an inflammatory response in the animal. In certain embodiments compounds are well tolerated by the animal. Increased tolerability can depend on a number of factors, including, but not limited to, the nucleotide sequence of the antisense compound, chemical modifications to the nucleotides, the particular motif of unmodified and modified nucleosides in the antisense compound, or combinations thereof. Tolerability may be determined by a number of factors. Such factors include body weight, organ weight, liver function, kidney function, platelet count, white blood cell count.

In certain embodiments, the compounds provided herein demonstrate minimal effect on organ weight. In certain embodiments, the compounds demonstrate less than a 7-fold, 6-fold, 5-fold, 4-fold, 3-fold, 2-fold or no significant increase in spleen and/or liver weight.

In certain embodiments, the compounds provided herein demonstrate minimal effect on liver function. Factors for the evaluation of liver function include ALT levels, AST levels, plasma bilirubin levels and plasma albumin levels. In certain embodiments the compounds provided herein demonstrate less than a 7-fold, less than a 6-fold, less than a 5-fold, less than a 4-fold, less than a 3-fold or less than a 2-fold or no significant increase in ALT or AST. In certain embodiments the compounds provided herein demonstrate less than a 3-fold, less than a 2-fold or no significant increase in plasma bilirubin levels.

In certain embodiments, the compounds provided herein demonstrate minimal effect on kidney function. In certain embodiments, the compounds provided herein demonstrate less than a 3-fold, less than a 2-fold, or no significant increase in plasma concentrations of blood urea nitrogen (BUN). In certain embodiments, the compounds provided herein demonstrate less than a 6-fold, 5-fold, 4-fold, 3-fold, 2-fold, or no significant increase in the ratio of urine protein to creatinine.

In certain embodiments, the compounds provided herein demonstrate minimal effect on hematological factors. In certain embodiments, the compounds provided herein demonstrate less than a 60%, 50%, 40%, 30%, 20%, 10% or 5% decrease in platelet count. In certain embodiments, the compounds provided herein demonstrate less than a 4-fold, less than a 3-fold, less than a 2-fold or no significant increase in monocyte count.

In certain embodiments compounds further display favorable pharmacokinetics. In certain embodiments, antisense compounds exhibit relatively high half-lives in relevant biological fluids or tissues.

In certain embodiments, compounds or compositions further display favorable viscosity. In certain embodiments, the viscosity of the compound or composition is no more than 40 cP at a concentration of 165-185 mg/mL.

In other embodiments, the compounds display combinations of the characteristics above and reduce factor 12 mRNA expression in an animal model with high efficiency.

Certain Indications

In certain embodiments, the invention provides methods of treating an individual comprising administering one or more pharmaceutical compositions of the present invention. In certain embodiments, the individual has a thromboembolic condition. In certain embodiments, the individual is at risk for a blood clotting disorder, including, but not limited to, infarct, thrombosis, embolism, thromboembolism such as deep vein thrombosis, pulmonary embolism, myocardial infarction, stroke, and mesenteric thrombosis. This includes individuals with an acquired problem, disease, or disorder that leads to a risk of thrombosis, for example, surgery, cancer, immobility, sepsis, atherosclerosis atrial fibrillation, as well as genetic predisposition, for example, antiphospholipid syndrome and the autosomal dominant condition, Factor V Leiden. In certain embodiments, the individual has been identified as in need of anticoagulation therapy. Examples of such individuals include, but are not limited to, those undergoing major orthopedic surgery (e.g., hip/knee replacement or hip fracture surgery) and patients in need of chronic treatment, such as those suffering from arterial fibrillation to prevent stroke. In certain embodiments the invention provides methods for prophylactically reducing Factor 12 expression in an individual. Certain embodiments include treating an individual in need thereof by administering to an individual a therapeutically effective amount of an antisense compound targeted to a Factor 12 nucleic acid.

In one embodiment, administration of a therapeutically effective amount of an antisense compound targeted to a Factor 12 nucleic acid is accompanied by monitoring of Factor 12 levels in the serum of an individual, to determine an individual's response to administration of the antisense compound. An individual's response to administration of the antisense compound is used by a physician to determine the amount and duration of therapeutic intervention.

In certain embodiments, administration of an antisense compound targeted to a Factor 12 nucleic acid results in reduction of Factor 12 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a Factor 12 nucleic acid results in a change in a measure of blood clotting as measured by a standard test, for example, but not limited to, activated partial thromboplastin time (aPTT) test, prothrombin time (PT) test, thrombin time (TCT), bleeding time, or D-dimer. In certain embodiments, administration of a Factor 12 antisense compound increases the measure by at least 15, 20, 25, 30, 35, 40, 45, 50, 55, 60, 65, 70, 75, 80, 85, 90, 95 or 99%, or a range defined by any two of these values. In some embodiments, administration of a Factor 12 antisense compound decreases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to Factor 12 are used for the preparation of a medicament for treating a patient suffering or susceptible to a thromboembolic condition.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions of the present invention. In certain embodiments, such one or more other pharmaceutical agents are designed to treat a different disease, disorder, or condition as the one or more pharmaceutical compositions of the present invention. In certain embodiments, such one or more other pharmaceutical agents are designed to treat an undesired side effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention are co-administered with another pharmaceutical agent to produce a combinational effect. In certain embodiments, one or more pharmaceutical compositions of the present invention are co-administered with another pharmaceutical agent to produce a synergistic effect.

In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include anticoagulant or antiplatelet agents. In certain embodiments, pharmaceutical agents that may be co-administered with a pharmaceutical composition of the present invention include NSAID/Cyclooxygenase inhibitors, such as, aspirin. In certain embodiments, pharmaceutical agents that may be co-administered with a pharmaceutical composition of the present invention include adenosine diphosphate (ADP) receptor inhibitors, such as, clopidogrel (PLAVIX) and ticlopidine (TICLID). In certain embodiments, pharmaceutical agents that may be co-administered with a pharmaceutical composition of the present invention include phosphodiesterase inhibitors, such as, cilostazol (PLETAL). In certain embodiments, pharmaceutical agents that may be co-administered with a pharmaceutical composition of the present invention include, glycoprotein IIB/IIIA inhibitors, such as, abciximab (REOPRO), eptifibatide (INTEGRILIN), tirofiban (AGGRASTAT), and defibrotide. In certain embodiments, pharmaceutical agents that may be co-administered with a pharmaceutical composition of the present invention include, adenosine reuptake inhibitors, such as, to dipyridamole (PERSANTINE). In certain embodiments, pharmaceutical agents that may be co-administered with a pharmaceutical composition of the present invention include, but are not limited to warfarin (and related coumarins), heparin, direct thrombin inhibitors (such as lepirudin, bivalirudin), apixaban, LOVENOX, and small molecular compounds that interfere directly with the enzymatic action of particular coagulation factors (e.g. rivaroxaban, which interferes with Factor Xa). In certain embodiments, pharmaceutical agents that may be co-administered with a Factor 12 specific inhibitor of the present invention include, but are not limited to, an additional Factor 12 inhibitor. In certain embodiments, the anticoagulant or antiplatelet agent is administered prior to administration of a pharmaceutical composition of the present invention. In certain embodiments, the anticoagulant or antiplatelet agent is administered following administration of a pharmaceutical composition of the present invention. In certain embodiments the anticoagulant or antiplatelet agent is administered at the same time as a pharmaceutical composition of the present invention. In certain embodiments the dose of a co-administered anticoagulant or antiplatelet agent is the same as the dose that would be administered if the anticoagulant or antiplatelet agent was administered alone. In certain embodiments the dose of a co-administered anticoagulant or antiplatelet agent is lower than the dose that would be administered if the anticoagulant or antiplatelet agent was administered alone. In certain embodiments the dose of a co-administered anticoagulant or antiplatelet agent is greater than the dose that would be administered if the anticoagulant or antiplatelet agent was administered alone.

In certain embodiments, the co-administration of a second compound enhances the anticoagulant effect of a first compound, such that co-administration of the compounds results in an anticoagulant effect that is greater, than the effect of administering the first compound alone. In other embodiments, the co-administration results in anticoagulant effects that are additive of the effects of the compounds when administered alone. In certain embodiments, the co-administration results in anticoagulant effects that are supra-additive of the effects of the compounds when administered alone. In certain embodiments, the co-administration of a second compound increases antithrombotic activity without increased bleeding risk. In certain embodiments, the first compound is an antisense compound. In certain embodiments, the second compound is an antisense compound.

In certain embodiments, an antidote is administered anytime after the administration of a Factor 12 specific inhibitor. In certain embodiments, an antidote is administered anytime after the administration of an antisense oligonucleotide targeting Factor 12. In certain embodiments, the antidote is administered minutes, hours, days, weeks, or months after the administration of an antisense compound targeting Factor 12. In certain embodiments, the antidote is a complementary (e.g. the sense strand) to the antisense compound targeting Factor 12. In certain embodiments, the antidote is a Factor 7, Factor 7a, Factor 12, or Factor 12a protein. In certain embodiments, the Factor 7, Factor 7a, Factor 12, or Factor 12a protein is a human Factor 7, human Factor 7a, human Factor 12, or human Factor 12a protein. In certain embodiments, the Factor 7 protein is NOVOSEVEN.

Certain Co-Administered Antiplatelet Therapies

In certain embodiments, Factor 12 inhibitors are combined with antiplatelet therapies. In certain embodiments, administration of a Factor 12 inhibitor in combination with an antiplatelet therapy results in little to no appreciable or detectable increase in risk of bleeding as compared to antiplatelet therapy alone. In certain embodiments, the risk profile or risk indications are unchanged over antiplatelet therapy alone.

The combination of antiplatelet and anticoagulant therapy is used in clinical practice most frequently in patients diagnosed with, for example, thromboembolism, atrial fibrillation, a heart valve disorder, valvular heart disease, stroke, CAD, and in patients having a mechanical valve. The benefit of dual therapy relates to the probable additive effect of suppressing both platelet and coagulation factor activities. The risk of dual therapy is the potential for increased bleeding (Dowd, M. Plenary Sessions/Thrombosis Research 123 (2008)).

Prior combinations of antiplatelet and anticoagulant therapy have been shown to increase the risk of bleeding compared with anticoagulant or antiplatelet therapy alone.

Such combinations include, FXa inhibitors (e.g., apixiban and rivaroxaban) with ADP receptor/P2Y12 inhibitors (Thienopyridines such as clopidogrel—also known as PLAVIX) and NSAIDs (e.g., aspirin and naproxen) (Kubitza, D. et al., *Br. J. Clin. Pharmacol.* 63:4 (2006); Wong, P. C. et al. *Journal of Thrombosis and Haemostasis* 6 (2008); FDA Advisory Committee Briefing Document for New Drug Application 22-406 (2009)). For example, Wong reports that addition of certain doses of apixaban to aspirin and to aspirin plus clopidogrel produced a significant increase in bleeding time compared with aspirin alone and aspirin plus clopidogrel. Kubitza reports that the combination administration of rivaroxaban and naproxen significantly increased bleeding time over naproxen alone.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1

Antisense Inhibition of Murine Factor 12 mRNA in Mouse Primary Hepatocytes

Antisense oligonucleotides targeted to a murine factor 12 nucleic acid were tested for their effects on Factor 12 mRNA in vitro. Cultured mouse primary hepatocytes at a density of 10,000 cells per well were transfected using Cytofectin reagent with 100 nM antisense oligonucleotide. After a treatment period of approximately 24 hours, RNA was isolated from the cells and mouse Factor 12 mRNA levels were measured by quantitative real-time PCR using the murine primer probe set RTS2959 (forward sequence CAAAGGAGGGACATGTATCAACAC, designated herein as SEQ ID NO: 4; reverse sequence CTGGCAATGTTTCCCAGTGA, designated herein as SEQ ID NO: 5; probe sequence CCCAATGGGCCACACTGTCTCTGC, designated herein as SEQ ID NO: 6). Factor 12 mRNA levels were adjusted according to total RNA content, as measured by RIBOGREEN. Results are presented as percent inhibition of Factor 12, relative to untreated control cells.

The chimeric antisense oligonucleotides in Table 1 were designed as 5-10-5 MOE gapmers. The gapmers are 20 nucleotides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Mouse target start site" indicates the 5'-most nucleoside to which the gapmer is targeted. "Mouse target stop site" indicates the 3'-most nucleoside to which the gapmer is targeted. The gapmers are targeted to mouse Factor 12 mRNA (GENBANK Accession No. NM_021489.2), incorporated herein as SEQ ID NO: 2.

TABLE 1

Inhibition of mouse Factor 12 mRNA levels by chimeric antisense oligonucleotides having 5-10-5 MOE wings and deoxy gap targeted to SEQ ID NO: 2

| Oligo ID | Mouse Target Start Site | Mouse Target Stop Site | Sequence | % inhibition | SEQ ID NO |
|---|---|---|---|---|---|
| 410944 | 980 | 999 | GCATGGGACAGAGATGGTGC | 68 | 7 |
| 410973 | 1842 | 1861 | GCACACAAGGAGGGAAGGAT | 96 | 8 |
| 410974 | 1858 | 1877 | CGTCCCATCCCAAGGAGCAC | 75 | 9 |
| 410975 | 1881 | 1900 | GTGACCCAGCATGCCACATT | 78 | 10 |

Example 2

Dose-Dependent Antisense Inhibition of Murine Factor 12 in Mouse Primary Hepatocytes Gapmers from Example 1, were tested at various doses in primary mouse hepatocytes. Cells were plated at density of 10,000 cells per well and transfected using cytofectin reagent with 6.25 nM, 12.5 nM, 25 nM, 50 nM, 100 nM, and 200 nM concentrations of antisense oligonucleotides, as specified in Table 2. After a treatment period of approximately 24 hours, RNA was isolated from the cells and murine Factor 12 mRNA levels were measured by quantitative real-time PCR. Murine Factor 12 mRNA levels were adjusted according to total RNA content, as measured by RIBOGREEN. Results are presented as percent inhibition of Factor 12, relative to untreated control cells. As illustrated in Table 2, Factor 12 mRNA levels were reduced in a dose-dependent manner.

TABLE 2

Dose-dependent antisense inhibition of murine Factor 12 in primary mouse hepatocytes

| Oligo ID | 6.25 nM | 12.5 nM | 25.0 nM | 50.0 nM | 100.0 nM | 200.0 nM | $IC_{50}$ (nM) |
|---|---|---|---|---|---|---|---|
| 410973 | 13 | 28 | 50 | 76 | 93 | 98 | 24.6 |
| 410975 | 0 | 0 | 5 | 28 | 68 | 93 | 66.8 |
| 410974 | 0 | 0 | 20 | 44 | 78 | 95 | 51.3 |
| 410944 | 0 | 0 | 8 | 24 | 62 | 94 | 71.4 |

Example 3

In Vivo Antisense Inhibition of Murine Factor 12

Antisense oligonucleotides from Example 2 targeted to murine Factor 12 mRNA (GENBANK Accession No. NM_021489.2, incorporated herein as SEQ ID NO: 2) showing statistically significant dose-dependent inhibition were evaluated in vivo.

Treatment

BALB/c mice were injected with 5 mg/kg, 10 mg/kg, 25 mg/kg, or 50 mg/kg of ISIS 410944, ISIS 410973, ISIS 410974, or ISIS 410975, administered subcutaneously twice a week for 3 weeks. A control group of mice was injected with phosphate buffered saline (PBS), administered subcutaneously twice a week for 3 weeks. Mice were sacrificed 5 days after receiving the last dose. Whole liver was harvested for RNA analysis and plasma was collected for clotting analysis (PT and aPTT) and protein analysis.

RNA Analysis

RNA was extracted from liver tissue for real-time PCR analysis of Factor 12. As shown in Table 3, the antisense oligonucleotides achieved dose-dependent reduction of murine Factor 12 over the PBS control. Results are presented as percent inhibition of Factor 12, relative to control.

TABLE 3

Dose-dependent antisense inhibition of murine Factor 12 mRNA in BALB/c mice

| Oligo ID | Dose (mg/kg) | % inhibition |
|---|---|---|
| 410944 | 5 | 65 |
|  | 10 | 80 |
|  | 25 | 89 |
|  | 50 | 92 |
| 410973 | 5 | 0 |
|  | 10 | 12 |
|  | 25 | 28 |
|  | 50 | 44 |
| 410974 | 5 | 8 |
|  | 10 | 43 |
|  | 25 | 75 |
|  | 50 | 80 |
| 410975 | 5 | 0 |
|  | 10 | 14 |
|  | 25 | 46 |
|  | 50 | 79 |

PT and aPTT Assay

Prothrombin Time (PT) and Activated Partial Thromboplastin Time (aPTT) were measured using platelet poor plasma (PPP) from mice treated with ISIS 410944 and ISIS 410975. PT and aPTT values provided in Table 4 are reported as International Normalized Ratio (INR) values. INR values for PT and aPTT were determined by dividing the PT or aPTT value for each experimental group (i.e. 5 mg/kg, 10 mg/kg, 25 mg/kg, and 50 mg/kg treatment with ISIS 410944 or ISIS 410975) by the PT or aPTT for the PBS treated group. This ratio was then raised to the power of the International Sensitivity Index (ISI) of the tissue factor used. As shown in Table 4, PT was not significantly prolonged in mice treated with ISIS 410944 or ISIS 410975. However, aPTT was prolonged in a dose-dependent manner in mice treated with ISIS 410944. These data suggest that antisense reduction of Factor 12 affects the contact activation pathway, but not the extrinsic pathway of blood coagulation.

TABLE 4

Effect of ISIS 410944 and ISIS 410975 on PT and aPTT in BALB/c mice

| ISIS no | Dose in mg/kg | PT INR | aPTT INR |
|---|---|---|---|
| 410944 | 5 | 1.03 | 1.06 |
|  | 10 | 1.04 | 1.06 |
|  | 25 | 1.02 | 1.14 |
|  | 50 | 1.03 | 1.20 |
| 410975 | 5 | 1.00 | 0.97 |
|  | 10 | 0.97 | 1.02 |
|  | 25 | 0.97 | 1.00 |
|  | 50 | 1.00 | 0.99 |

Protein Analysis

Factor 12 proenzyme from the plasma of mice treated with ISIS 410944, was measured using a F12 assay based on clotting time. Clotting times were determined in duplicate with a ST4 semi-automated coagulation instrument (Diagnostica Stago, N.J.). Thirty µl of citrated sample plasma diluted 1/20 in HEPES-NaCl buffer with BSA was incubated with 30 µl aPTT reagent (Platelet Factor 3 reagent plus particulate activator, BioMerieux, N.C.) and 30 µl of citrated plasma deficient of Factor 12 (human congenital, George King Bio-Medical Inc.) at 37° C. for 5 min. This was followed by the addition of 30 µL of 25 mM $CaCl_2$ at 37° C. to initiate clotting. Results, in seconds, were interpolated on a standard curve of serially diluted citrated control murine plasma.

As shown in Table 5, treatment with ISIS 410944 resulted in a significant dose-dependent reduction of Factor 12 protein. Results are presented as percent inhibition of Factor 12, relative to PBS control.

TABLE 5

Dose-dependent inhibition of murine Factor 12 protein by ISIS 410944 in BALB/c mice

| Dose (mg/kg) | % inhibition |
|---|---|
| 5 | 61 |
| 10 | 74 |
| 25 | 90 |
| 50 | 96 |

Example 4

Antisense Inhibition of Rat Factor 12 mRNA in Rat Primary Hepatocytes

Antisense oligonucleotides targeted to a rat factor 12 nucleic acid were tested for their effects on Factor 12 mRNA in vitro. Cultured rat primary hepatocytes at a density of 20,000 cells per well were transfected using Cytofectin reagent with 200 nM antisense oligonucleotide. After a treatment period of approximately 24 hours, RNA was isolated from the cells and rat Factor 12 mRNA levels were measured by quantitative real-time PCR using the rat primer probe set RTS3314 (forward sequence GGGCCACCACGCATTCT, designated herein as SEQ ID NO: 11; reverse sequence CGC-CACTCCAGACGTAGCA, designated herein as SEQ ID NO: 12; probe sequence CCGGAACCCAGATAATGACA-CACGTCC, designated herein as SEQ ID NO: 13). Factor 12 mRNA levels were adjusted according to total RNA content, as measured by RIBOGREEN. Results are presented as percent inhibition of Factor 12, relative to untreated control cells.

The chimeric antisense oligonucleotides in Table 6 were designed as 5-10-5 MOE gapmers. The gapmers are 20 nucleotides in length, wherein the central gap segment is comprised of ten 2'-deoxynucleosides and is flanked on both sides (in the 5' and 3' directions) by wings comprising 5 nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Rat target start site" indicates the 5'-most nucleotide to which the gapmer is targeted. "Rat target stop site" indicates the 3'-most nucleotide to which the gapmer is targeted. All the gapmers were targeted to rat Factor 12 mRNA (GENBANK Accession No. NM_001014006.1), incorporated herein as SEQ ID NO: 3.

Table 7. After a treatment period of approximately 24 hours, RNA was isolated from the cells and rat Factor 12 mRNA levels were measured by quantitative real-time PCR. Rat factor 12 mRNA levels were adjusted according to total RNA content as measured by RIBOGREEN. Results are presented as percent inhibition of Factor 12, relative to untreated control cells. As illustrated in Table 7, Factor 12 mRNA levels were reduced in a dose-dependent manner.

TABLE 7

Dose-dependent antisense inhibition of rat Factor 12 in rat primary hepatocytes

| Oligo ID | 12.5 nM | 25.0 nM | 50.0 nM | 100.0 nM | 200.0 nM | IC$_{50}$ (nM) |
|---|---|---|---|---|---|---|
| 486600 | 38 | 46 | 44 | 63 | 80 | 31.4 |
| 486723 | 0 | 21 | 46 | 71 | 85 | 59.5 |
| 486608 | 37 | 57 | 61 | 76 | 70 | 22.5 |
| 486675 | 24 | 26 | 40 | 55 | 71 | 73.3 |
| 486724 | 16 | 7 | 49 | 63 | 73 | 58.4 |
| 486647 | 3 | 18 | 30 | 48 | 75 | 91.7 |

Example 6

In Vivo Antisense Inhibition of Rat Factor 12

Antisense oligonucleotides from Example 5 targeted to rat Factor 12 mRNA (GENBANK Accession No. NM_001014006.1, incorporated herein as SEQ ID NO: 3) showing statistically significant dose-dependent inhibition were evaluated in vivo.

Treatment

Male Sprague Dawley rats were injected with 50 mg/kg of ISIS 486600, ISIS 486608, ISIS 486647, ISIS 486675, ISIS 486723, or ISIS 486724 administered subcutaneously twice a week for 4 weeks. A control group of rats was injected with phosphate buffered saline (PBS) administered subcutaneously twice a week for 4 weeks. Rats were sacrificed 3 days after receiving the last dose. Whole liver was harvested for RNA analysis and plasma was collected analysis.

RNA Analysis

RNA was extracted from liver tissue for real-time PCR analysis of Factor 12. As shown in Table 8, the antisense oligonucleotides achieved significant reduction of rat Factor 12 over the PBS control. Results are presented as percent inhibition of Factor 12, relative to control.

TABLE 6

Inhibition of rat Factor 12 mRNA levels by chimeric antisense oligonucleotides having 5-10-5 MOE wings and deoxy gap targeted to SEQ ID NO: 3

| Oligo ID | Rat Target Start Site | Rat Target Stop Site | Sequence | % inhibition | SEQ ID NO |
|---|---|---|---|---|---|
| 486600 | 578 | 597 | GGCAATGTTTCCCGGTGAGG | 87 | 14 |
| 486608 | 832 | 851 | CGCCTTAAGGTCTAAGTCGC | 85 | 15 |
| 486647 | 1958 | 1977 | CGTCAGTGTAGACCCCGGGC | 80 | 16 |
| 486675 | 568 | 587 | CCCGGTGAGGTGTTCAGGGC | 82 | 17 |
| 486723 | 2025 | 2044 | TCGCAAGGACCGACCCTGGT | 88 | 18 |
| 486724 | 2041 | 2060 | GGCCCAGCCACTAGCTTCGC | 81 | 19 |

Example 5

Dose-Dependent Antisense Inhibition of Rat Factor 12 in Rat Primary Hepatocytes Gapmers from Example 4, were tested at various doses in rat primary hepatocytes. Cells were plated at a density of 20,000 cells per well and transfected using cytofectin reagent with 12.5 nM, 25.0 nM, 50.0 nM, 100.0 nM, and 200.0 nM concentrations of antisense oligonucleotides, as specified in

TABLE 8

Antisense inhibition of rat Factor
12 mRNA in Sprague Dawley rats

| Oligo ID | % inhibition |
| --- | --- |
| 486600 | 91 |
| 486608 | 98 |
| 486647 | 99 |
| 486675 | 74 |
| 486723 | 99 |
| 486724 | 98 |

Metabolic Tolerability

To evaluate the effect of ISIS oligonucleotides on metabolic tolerability in rats, plasma concentrations of alanine transaminase (ALT), aspartate transaminase (AST), BUN, creatinine, and albumin were measured using an automated clinical chemistry analyzer (Hitachi Olympus AU400e, Melville, N.Y.). The results are presented in Table 9 and demonstrate that treatment with most of the ISIS oligonucleotides had minimal effect on tolerability markers in rats.

TABLE 9

Effect of antisense oligonucleotide treatment
on metabolic markers in Sprague Dawley rats

|  | ALT | AST | BUN | Albumin | Creatinine |
| --- | --- | --- | --- | --- | --- |
| PBS | 40 | 86 | 17 | 2.55 | 0.45 |
| 486600 | 76 | 125 | 23 | 3.08 | 0.52 |
| 486608 | 105 | 196 | 18 | 3.52 | 0.49 |
| 486647 | 86 | 154 | 21 | 3.88 | 0.52 |
| 486675 | 247 | 377 | 23 | 4.43 | 0.60 |
| 486723 | 120 | 206 | 22 | 3.13 | 0.61 |
| 486724 | 59 | 118 | 21 | 3.34 | 0.66 |

Body and Organ Weights

The body weights of the rats were measured pre-dose and at the end of the treatment period. The body weights are presented in Table 10, and are expressed as percent increase over the PBS control weight taken before the start of treatment. Liver, spleen and kidney weights were measured at the end of the study, and are also presented in Table 10 as a percentage change over the respective organ weights of the PBS control.

TABLE 10

Change in body and organ weights of Sprague-Dawley
rats after antisense oligonucleotide treatment (%)

|  | Body weight | Liver | Kidney | Spleen |
| --- | --- | --- | --- | --- |
| PBS | 70 | — | — | — |
| 486600 | 31 | −6 | −14 | 131 |
| 486608 | 58 | 13 | −4 | 47 |
| 486647 | 46 | 21 | −3 | 58 |
| 486675 | 67 | 26 | 2 | 25 |
| 486723 | 46 | 7 | −14 | 50 |
| 486724 | 50 | 22 | −15 | 47 |

Example 7

In Vivo Effect of Antisense Inhibition of Murine Factor 12 in the FeCl$_3$ Induced Venous Thrombosis (VT) Model ISIS 410944 (SEQ ID NO: 7) was evaluated in the FeCl$_3$ induced VT mouse model.

Treatment

Six groups of 8 BALB/c mice each were treated with 1.25 mg/kg, 2.50 mg/kg, 5.00 mg/kg, 10.00 mg/kg, 20.00 mg/kg, or 40.00 mg/kg of ISIS 410944, administered subcutaneously twice a week for 3 weeks. Two control groups of 12 BALB/c mice each were treated with PBS, administered subcutaneously twice a week for 3 weeks. Two days after the last dose of ISIS 410944 or PBS, mice of all groups were anesthetized with 150 mg/kg ketamine mixed with 10 mg/kg xylazine, administered by intraperitoneal injection. Thrombus formation was induced with FeCl$_3$ in all groups of anesthetized mice except the first control group.

In mice undergoing FeCl$_3$ treatment, thrombus formation was induced by applying a piece of filter paper (2×4 mm) pre-saturated with 10% FeCl$_3$ solution directly on the vena cava. After 3 minutes of exposure, the filter paper was removed. Thirty minutes after the filter paper application, a fixed length of the vein containing the thrombus was dissected out for platelet analysis. Liver was collected for RNA analysis.

RNA Analysis

RNA was extracted from liver tissue for real-time PCR analysis of Factor 12. Results are presented as percent inhibition of Factor 12, relative to PBS control. As shown in Table 11, treatment with ISIS 410944 resulted in significant dose-dependent reduction of Factor 12 mRNA in comparison to the PBS control.

TABLE 11

Dose-dependent reduction of Factor 12 mRNA in
the FeCl$_3$ induced venous thrombosis model

| Dose (mg/kg) | % inhibition |
| --- | --- |
| 1.25 | 24 |
| 2.50 | 48 |
| 5.00 | 67 |
| 10.00 | 78 |
| 20.00 | 86 |
| 40.00 | 99 |

Quantification of Platelet Composition

Real-time PCR quantification of platelet factor-4 (PF-4) was used to quantify platelets in the vena cava as a measure of thrombus formation. Results are presented as a percentage of PF-4 in ISIS 410944-treated mice, as compared to the two PBS-treated control groups. As shown in Table 12, treatment with ISIS 410944 resulted in a dose-dependent reduction of PF-4 in comparison to the PBS control. Therefore, reduction of Factor 12 by the compounds provided herein is useful for inhibiting thrombus and clot formation.

TABLE 12

Analysis of thrombus formation by real-time PCR quantification
of PF-4 in the FeCl$_3$ induced venous thrombosis model

|  | Dose in mg/kg | PF-4 |
| --- | --- | --- |
| PBS − FeCl$_3$ | — | 0 |
| PBS + FeCl$_3$ | — | 100 |
| ISIS 410944 | 1.25 | 69 |
|  | 2.50 | 66 |
|  | 5.00 | 79 |
|  | 10.00 | 47 |
|  | 20.00 | 46 |
|  | 40.00 | 39 |

Example 8

In Vivo Effect of Antisense Inhibition of Murine Factor 12 in a Tail Bleeding Assay Tail-bleeding was measured to observe whether treatment with ISIS 410944 causes internal hemorrhage in mice.

Treatment

Six groups of 8 BALB/c mice each were treated with 1.25 mg/kg, 2.50 mg/kg, 5.00 mg/kg, 10.00 mg/kg, 20.00 mg/kg, or 40.00 mg/kg of ISIS 410944, administered subcutaneously twice a week for 3 weeks. A control group of 8 BALB/c mice was treated with PBS, administered subcutaneously twice a week for 3 weeks.

Tail-Bleeding Assay

Two days after the final treatment of ISIS 410944 or PBS, mice were placed in a tail bleeding chamber. Mice were anesthetized in the chamber with isoflurane and a small piece of tail (approximately 4 mm from the tip) was cut with sterile scissors. The tail cut was immediately placed in a 15 mL Falcon tube filled with approximately 10 mL of 0.9% NaCl buffer solution warmed to 37° C. The blood was collected over the course of 40 minutes. The saline filled tubes were weighed both before and after bleeding. The results are provided in Table 13.

Treatment with ISIS 410944 did not affect bleeding as compared to PBS treated mice. These data suggest that the hemorrhagic potential of the compounds provided herein is low. These data taken with the results provided in Example 7 suggest inhibition of Factor 12 with the compounds described herein are useful for providing antithrombotic activity without associated bleeding risk.

TABLE 13

Tail bleeding assay after treatment with ISIS 410944

|  | Dose (mg/kg) | Blood (g) |
|---|---|---|
| PBS | — | 0.08 |
| ISIS 410944 | 1.25 | 0.06 |
|  | 2.50 | 0.06 |
|  | 5.00 | 0.05 |
|  | 10.00 | 0.03 |
|  | 20.00 | 0.04 |
|  | 40.00 | 0.03 |

Example 9

In Vivo Effect of Antisense Inhibition of Murine Factor 12 in the FeCl$_3$ Induced Abdominal Aortic Thrombosis Model ISIS 410944 (SEQ ID NO: 7) was evaluated in the FeCl$_3$ induced abdominal aortic thrombosis mouse model.

Treatment

Three groups of 8 BALB/c mice each were treated with 10 mg/kg, 20 mg/kg, or 40 mg/kg of ISIS 410944, administered subcutaneously twice a week for 3 weeks. One day after receiving the last dose of ISIS 410944, mice were anesthetized with a subcutaneous injection of ketamine (75 mg/kg) mixed with xylazine (25 mg/kg). The aorta was exposed via a midline incision through the abdomen followed by retraction of intestines. The aorta was carefully dissected away from the inferior vena cava for a distance of 2-3 mm immediately inferior to the renal arteries. The exposed aorta was topically bathed in a 10% FeCl$_3$ solution for 20 min, after which the mice were euthanized by cervical dislocation. The aorta was removed for further analysis.

Two control groups of 8-10 BALB/c mice each were treated with PBS, administered subcutaneously twice a week for 3 weeks. One of the control groups was subjected to similar surgery, as described above. Both control groups were euthanized by cervical dislocation, and the aorta from each mouse was removed for further analysis.

RNA Analysis

RNA was extracted from liver tissue for real-time PCR analysis of Factor 12. Results are presented as percent inhibition of Factor 12, relative to PBS control. As shown in Table 14, treatment with ISIS 410944 resulted in significant dose-dependent reduction of Factor 12 mRNA in comparison to the PBS control.

TABLE 14

Dose-dependent reduction of Factor 12 mRNA in the FeCl$_3$ induced abdominal aortic thrombosis model

| Dose (mg/kg) | % inhibition |
|---|---|
| 10 | 67 |
| 20 | 74 |
| 40 | 83 |

Quantification of Platelet Composition

Real-time PCR quantification of platelet factor-4 (PF-4) was used to quantify platelets in the aorta as a measure of thrombus formation. Results are presented as a percentage of PF-4 in ISIS 410944-treated mice, as compared to the two PBS-treated control groups. As shown in Table 15, treatment with ISIS 410944 resulted in a dose-dependent reduction of PF-4 in comparison to the PBS control. Therefore, reduction of Factor 12 by the compounds provided herein is useful for inhibiting thrombus and clot formation.

TABLE 15

Analysis of thrombus formation by real-time PCR quantification of PF-4 in the FeCl$_3$ induced abdominal aortic thrombosis model

|  | Dose in mg/kg | PF-4 |
|---|---|---|
| PBS – FeCl$_3$ | — | 0 |
| PBS + FeCl$_3$ | — | 100 |
| ISIS 410944 | 10 | 59 |
|  | 20 | 33 |
|  | 40 | 18 |

Example 10

In Vivo Effect of Antisense Inhibition of Murine Factor 12 in a Stenosis-Induced Inferior Vena Cava Thrombosis Model ISIS 410944 (SEQ ID NO: 7) was evaluated in a stenosis-induced inferior vena cava thrombosis mouse model.

Treatment

Four groups of 8 BALB/c mice each were treated with 5 mg/kg, 10 mg/kg, 20 mg/kg, or 40 mg/kg of ISIS 410944, administered subcutaneously twice a week for 3 weeks. One day after receiving the last dose of ISIS 410944, mice were anesthetized with 2.5% inhalant isoflurane. The inferior vena cava (IVC) was exposed via a midline abdominal incision below the left renal vein, and separated from the abdominal aorta by blunt dissection. A 6-0 silk tie (Ethicon, UK) was placed behind the vessel just below the left renal vein and 2 silk sutures (4-0, Ethicon, UK) were placed longitudinally over the IVC and tied over the top. The 4-0 sutures were then removed. Two neurovascular surgical clips (Braun Medical) were applied at two separate positions below the ligation for twenty seconds each. Finally, the bowel was placed back into the abdominal cavity and the laparotomy was closed. The IVC was collected 24 hrs after the surgery.

Two control groups of 8-10 BALB/c mice each were treated with PBS, administered subcutaneously twice a week for 3 weeks. One of the control groups was subjected to similar surgery, as described above. IVC from both control groups was removed for further analysis.

RNA Analysis

RNA was extracted from liver tissue for real-time PCR analysis of Factor 12. Results are presented as percent inhibition of Factor 12, relative to PBS control. As shown in Table 16, treatment with ISIS 410944 resulted in significant dose-dependent reduction of Factor 12 mRNA in comparison to the PBS control.

TABLE 16

Dose-dependent reduction of Factor 12 mRNA in the stenosis-induced IVC thrombosis model

| Dose (mg/kg) | % inhibition |
|---|---|
| 5 | 52 |
| 10 | 60 |
| 20 | 69 |
| 40 | 76 |

Measurement of Thrombus

IVC containing thrombus was weighed in each treatment group and PBS control group. The data is presented in Table 17 and demonstrates the reduction of thrombus formation in mice treated with ISIS 410944 compared to the control.

TABLE 17

Weight of the thrombus (mg) in the stenosis-induced IVC thrombosis model

| | Dose (mg/kg) | Thrombus weight (mg) |
|---|---|---|
| PBS | — | 17.1 |
| ISIS 410944 | 5 | 16.5 |
| | 10 | 15.2 |
| | 20 | 15.3 |
| | 40 | 4.9 |

Example 11

In Vivo Effect of Antisense Inhibition of Murine Factor 12 in a Thromboplastin-Induced Pulmonary Embolism Model ISIS 410944 (SEQ ID NO: 7) was evaluated in a thromboplastin-induced pulmonary embolism mouse model.

Treatment

A group of 8 BALB/c mice was treated with 40 mg/kg of ISIS 410944, administered subcutaneously twice a week for 3 weeks. A control group of 8 BALB/c mice were administered PBS injected subcutaneously twice a week for 3 weeks. Four mice each from the treatment and control groups were treated with the Neoplastine form of thromboplastin, and the remaining four mice from the treatment and control groups were treated with the Triniclot form. Either form of thromboplastin was injected into the inferior vena cava (IVC). Triniclot (Thrombomax) was resuspended in 80 mL PBS and 4 µL/g body weight was injected. For Neoplastin, 100 µl of a 1:4 dilution of STA-Neoplastin CI Plus (~1 nM tissue factor, Diagnostica Stago, Asnières sur Seine, France) was infused into the IVC over thirty seconds. The time of death in all cases was recorded, which was, on average, 20 min after the injection. While the mice were in respiratory arrest but the heart was still beating, 0.5 ml Evans blue solution (1% in PBS) was injected in the IVC. Lungs were excised, photographed and scored for Evans blue perfusion defects. Time to cessation of breathing was determined. Any mice that survived thromboplastin infusion were sacrificed by pentobarbital overdose.

RNA Analysis

RNA was extracted from liver tissue for real-time PCR analysis of Factor 12. Results are presented as percent inhibition of Factor 12, relative to PBS control. Treatment with 40 mg/kg of ISIS 410944 resulted in an 87% reduction of Factor 12 mRNA in comparison to the PBS control.

Measurement of Time to Death

The time taken for the mice to die after injection of thromboplastin was measured and is presented in Table 18. The time to death of mice treated with ISIS 410944 was prolonged compared to the PBS control.

TABLE 18

Time to death of mice in the stenosis-induced IVC thrombosis model

| | Thromboplastin form | Time to death (sec) |
|---|---|---|
| PBS | Triniclot | 133 |
| | Neoplastine | 185 |
| ISIS 410944 | Triniclot | 155 |
| | Neoplastine | 215 |

Lung Score and Measurement of Evan's Dye Uptake

The lungs, which were perfused with Evan's Blue dye, were scored for Evan's blue perfusion defects. The scoring system was from 0-4, with '0' designated for intact lungs which were heavily stained with dye and '4' designated for lungs with high perfusion defects which retained very little dye. The data is presented in Table 32 and demonstrates that the lungs in the PBS control had a high score, due to severe perfusion defects, whereas the lungs from the treatment group had a significantly lower score, indicating that treatment with ISIS 410944 resulted in less pulmonary embolism compared to the PBS control.

After the scoring, the lungs were placed in formamide solution to leach out the dye. The color intensity of the dye-infused formamide solution was then measured at $OD_{600nm}$, and is also presented in Table 19. The $OD_{600nm}$ of the formamide solution from oligonucleotide treated group was higher than that of the PBS control group, since the lungs from mice treated with ISIS 410944 were significantly more intact than that of the PBS control group.

TABLE 19

Lung scores and $OD_{600\,nm}$ of Evan's Blue dye in the stenosis-induced IVC thrombosis model

| | Thromboplastin form | Lung score | $OD_{600\,nm}$ |
|---|---|---|---|
| PBS | Triniclot | 3.8 | 0.4 |
| | Neoplastine | 3.3 | 0.4 |
| ISIS 410944 | Triniclot | 2.3 | 1.7 |
| | Neoplastine | 2.3 | 1.6 |

Example 12

In Vivo Effect of Antisense Inhibition of Murine Factor 12 in the FeCl₃ Induced Mesenteric Thrombosis Model ISIS 410944 was evaluated in the $FeCl_3$ induced mesenteric thrombosis mouse model.

Treatment

Groups of 6-8 Swiss-Webster mice each were treated with 5 mg/kg, 10 mg/kg, 20 mg/kg, or 40 mg/kg of ISIS 410944, administered subcutaneously twice a week for 3 weeks (weekly doses of 10 mg/kg, 20 mg/kg, 40 mg/kg, or 80 mg/kg, respectively). A control group of 6 Swiss-Webster mice was treated with PBS, administered subcutaneously twice a week for 3 weeks. Two days after the last dose of antisense oligonucleotide or PBS, mice of all groups were anesthetized with 75 mg/kg ketamine mixed with 25 mg/kg xylazine, administered by intraperitoneal injection.

Rhodamine 6G dye was injected subcutaneously at 5 mg/kg to stain platelets. Alexa-647-labeled anti-fibrinogen antibody at a dosage of 1 mg/kg was injected via tail vein to stain fibrin. The abdomen was opened by a mid-section incision. The visceral mesentery was spread on a glass coverslip and the mesenteric arterioles were located by observation under a microscope. Thrombus formation was induced by applying cotton threads (2×0.3 mm) pre-saturated with 6% $FeCl_3$ solution directly on the target vessel. After three minutes of exposure, the thread was removed and color intensities of both the dyes were recorded by fluorescent microscopy (Olympus FluoView 1000 confocal laser scanning microscope) with appropriate filters for 70 min.

The results for the measurement of fluorescent intensity for platelet aggregation in the control and treatment groups are presented in Table 20, expressed in arbitrary units (a.u.). Platelet aggregation was reduced in mice treated with ISIS 410944 at doses of 20 mg/kg/week and higher as compared to mice treated with PBS. The results for the measurement of fluorescent intensity for fibrin formation in the control and treatment groups are presented in Table 21, also expressed in arbitrary units (a.u.). Fibrin formation was reduced in mice treated with ISIS 410944 at a dose of 20 mg/kg/week as compared to mice treated with PBS. Therefore, these results suggest that ISIS 410944 inhibits thrombus formation.

TABLE 20

Analysis of platelet aggregation by real-time measurement of fluorescent intensity (a.u.) in a $FeCl_3$ induced mesenteric thrombus model

| Time (sec) | PBS | 10 mg/kg/wk | 20 mg/kg/wk | 40 mg/kg/wk | 80 mg/kg/wk |
|---|---|---|---|---|---|
| 752 | 213 | 90 | 0 | 13 | 53 |
| 1018 | 149 | 2 | 283 | 4 | 0 |
| 1284 | 393 | 486 | 501 | 47 | 7 |
| 1550 | 634 | 1003 | 508 | 142 | 11 |
| 1815 | 1062 | 1306 | 499 | 120 | 16 |
| 2081 | 1160 | 1305 | 545 | 182 | 16 |
| 2347 | 1729 | 1951 | 640 | 140 | 91 |
| 2613 | 1867 | 2107 | 506 | 175 | 26 |
| 2879 | 1880 | 2101 | 782 | 328 | 48 |
| 3144 | 2060 | 2127 | 677 | 288 | 88 |
| 3410 | 2083 | 2359 | 785 | 252 | 25 |
| 3676 | 2119 | 2325 | 836 | 212 | 8 |
| 3944 | 2217 | 2312 | 877 | 218 | 0 |

TABLE 21

Analysis of fibrin formation by real-time measurement of fluorescent intensity (a.u.) in a $FeCl_3$ induced mesenteric thrombus model

| Time (sec) | PBS | 10 mg/kg/wk | 20 mg/kg/wk | 40 mg/kg/wk | 80 mg/kg/wk |
|---|---|---|---|---|---|
| 752 | 9 | 35 | 0 | 22 | 46 |
| 1018 | 86 | 0 | 42 | 59 | 5 |
| 1284 | 203 | 83 | 5 | 126 | 17 |
| 1550 | 319 | 132 | 81 | 165 | 18 |
| 1815 | 491 | 436 | 229 | 149 | 0 |
| 2081 | 575 | 649 | 252 | 205 | 16 |
| 2347 | 815 | 703 | 271 | 233 | 0 |
| 2613 | 957 | 905 | 290 | 157 | 0 |
| 2879 | 1186 | 1029 | 324 | 307 | 0 |
| 3144 | 1112 | 1047 | 348 | 259 | 7 |
| 3410 | 1398 | 1104 | 362 | 276 | 16 |
| 3676 | 1681 | 2325 | 432 | 256 | 0 |
| 3944 | 1893 | 1156 | 427 | 293 | 0 |

What is claimed is:

1. A method of treating an animal having a thromboembolic condition or at risk for developing a thromboembolic condition comprising administering to the animal a therapeutically effective amount of a compound comprising an oligonucleotide consisting of 12-25 linked nucleosides targeted to a Factor 12 nucleic acid, wherein the oligonucleotide has a nucleobase sequence that is at least 90% complementary to SEQ ID NO: 1, SEQ ID NO: 2, or SEQ ID NO: 3 as measured over the entirety of the oligonucleotide, wherein said compound does not significantly increase bleeding risk in the animal.

2. The method of claim 1, wherein the thromboembolic condition is any of deep vein thrombosis, pulmonary embolism, myocardial infarction, stroke, mesenteric thrombosis, or a combination thereof.

3. The method of claim 1, wherein the animal is a human.

4. The method of claim 2, wherein the administering inhibits thrombus and clot formation.

5. The method of claim 2, wherein the administering prolongs aPTT.

6. The method of claim 2, wherein the administering does not prolong PT.

7. The method of claim 2, wherein the administering prolongs aPTT and does not prolong PT.

8. The method of claim 2, wherein the administering decreases Platelet Factor 4 (PF-4).

9. The method of claim 2, wherein the administering increases time for thrombus formation.

10. The method of claim 1, wherein the oligonucleotide has a nucleobase sequence that is 100% complementary to SEQ ID NO: 1, SEQ ID NO: 2, or SEQ ID NO: 3 as measured over the entirety of the oligonucleotide.

11. The method of claim 1, wherein the oligonucleotide comprises at least one modified internucleoside linkage.

12. The method of claim 11, wherein the at least one modified internucleoside linkage is a phosphorothioate internucleoside linkage.

13. The method of claim 12, wherein at least one nucleoside of the oligonucleotide comprises a modified sugar.

14. The method of claim 13, wherein the modified sugar is a bicyclic sugar or a 2'-O-methoxyethyl modified sugar.

15. The method of claim 14, wherein the bicyclic sugar comprises a 4'-CH(CH$_3$)—O-2' bridge.

16. The method of claim 14, wherein at least one nucleoside of the oligonucleotide comprises a modified nucleobase.

17. The method of claim 16, wherein the modified nucleobase is a 5-methylcytosine.

18. The method of claim 1, wherein the oligonucleotide comprises:
- a gap segment consisting of linked deoxy nucleosides;
- a 5' wing segment consisting of linked nucleosides;
- a 3' wing segment consisting of linked nucleosides;
- wherein the gap segment is positioned between the 5' wing segment and the 3' wing segment and wherein each nucleoside of each wing segment comprises a modified sugar.

19. The method of claim 18, wherein the oligonucleotide comprises:
- a gap segment consisting of ten linked deoxynucleosides;
- a 5' wing segment consisting of five linked nucleosides;
- a 3' wing segment consisting of five linked nucleosides;
- wherein the gap segment is positioned immediately adjacent to and between the 5' wing segment and the 3' wing segment, wherein each nucleoside of each wing segment comprises a 2'-O-methoxyethyl sugar, wherein each cytosine in the oligonucleotide is a 5-methylcytosine, and wherein each internucleoside linkage of the oligonucleotide is a phosphorothioate linkage.

20. The method of claim 19, wherein the oligonucleotide consists of 20 linked nucleosides.

21. The method of claim 1, wherein said compound is a single-stranded oligonucleotide.

* * * * *